United States Patent [19]

Sugino et al.

[11] Patent Number: 6,132,988
[45] Date of Patent: Oct. 17, 2000

[54] DNA ENCODING A NEURONAL CELL-SPECIFIC RECEPTOR PROTEIN

[75] Inventors: Hiromu Sugino; Takanori Nakamura; Hiroki Shouji, all of Tokushima, Japan

[73] Assignee: Takeda Chemical Industries, Ltd., Osaka, Japan

[21] Appl. No.: 08/738,168

[22] Filed: Oct. 25, 1996

[30] Foreign Application Priority Data

Oct. 27, 1995 [JP] Japan ..................................... 7-280939
Jul. 4, 1996 [JP] Japan ..................................... 8-174909

[51] Int. Cl.⁷ ........................... C12N 15/12; C12N 15/63; C12N 15/85
[52] U.S. Cl. ..................... 435/69.1; 435/325; 435/320.1; 435/252.1; 536/23.1; 536/23.5
[58] Field of Search .................................. 536/23.1, 23.5; 435/69.1, 325, 320.1, 252.1

[56] References Cited

FOREIGN PATENT DOCUMENTS 0771873  6/1997  European Pat. Off. .
WO 92/20793  11/1992  WIPO .

OTHER PUBLICATIONS

J. Xu et al., "Inhibin Antagonizes Inhibition of Liver Cell Growth by Activin by a Dominant–negative Mechanism," J. Biol. Chem. 270:6308–6313 (1995).

Matthews, et al., "Expression Cloning of an Activin Receptor, A predicted Transmembrane Serine Kinase", Cell 65:973–982 (1991).

*Primary Examiner*—Anthony C. Caputa
*Assistant Examiner*—Robert C Hayes
*Attorney, Agent, or Firm*—David G. Conlin; Robert L. Buchanan; Dike, Bronstein, Roberts & Cushman, LLP

[57] ABSTRACT

To provide a method of isolating and detecting a new receptor gene, as a means of elucidating the function of neuronal cell-specific receptors, especially of elucidating the detailed mechanism of the neuronal cell differentiation inhibitory and nerve nutrition factor-like actions of activin receptors, DNA containing said new receptor gene, a method of producing a protein encoded by this new receptor gene, and use for this DNA and protein. The receptor protein of the present invention and DNA encoding this protein can be used for various purposes, including 1) ligand determination, 2) obtainment of antibodies and antisera, 3) construction of recombinant receptor protein expression systems, 4) development of receptor binding assay systems and screening for pharmaceutical candidate compounds using expression systems, 5) drug designing based on comparison with structurally similar ligand receptors, 6) reagent for preparation of probes and PCR primers for gene diagnosis, and 7) drug for gene therapy.

9 Claims, 13 Drawing Sheets

```
451  AAATCCTGTTACACCGAAGCCACCCTATTACACAACATTCTGCTGTACCACTAATGTTAATTGCAGGAATTGTCATTTGTGC    540
109   N  P  V  T  P  K  P  P  Y  Y  N  I  L  L  Y  S  L  V  P  L  M  L  I  A  G  I  V  I  C  A    138

541  ATTTGGGTGTACAGACATCACAAGATGGCCTACCCTCCTGTTCCTACTCAAGACCCAGGACCACCTCCCACCTTCCCCATTACT    630
139   F  W  V  Y  R  H  H  K  M  A  Y  P  P  V  L  V  P  T  Q  D  P  G  P  P  P  P  S  P  L  L    168

631  AGGGTTGAAGCCATTGCAGCTGTGTTAGAAGTGAAAGCAAGGGGAAGATTTGGTGTGTCTGGAAAGCCCAGTTGCTCAATGATATGTGGC    720
169   G  L  K  P  L  Q  L  L  E  V  K  A  R  G  R  F  G  C  V  W  K  A  Q  L  L  N  E  Y  V  A    198

721  TGTCAAAATATTCCAATACAGGACAAACAGTCCTGGCAGAATGAATGAAGTCTATAGTCTACCTGGAATGAAGCATGAGAACATACT    810
199   V  K  I  F  P  I  Q  D  K  Q  S  W  Q  N  E  Y  E  V  Y  S  L  P  G  M  K  H  E  N  I  L    228

811  ACAGTTCATTGGTGCAGAGAAAAGAGGCACCAGTGTGGATGTGGACCTGTGGCTAATCACAGCATTTCATGAAAGGGCTCACTGTCAGA    900
229   Q  F  I  G  A  E  K  R  G  T  S  V  D  V  D  L  W  L  I  T  A  F  H  E  K  G  S  L  S  D    258

901  CTTTCTTAAGGCTAATGTGGTCTCTTGGAATGAACTTGTCATATTGCAGAGATTGGCATATTTACATGAGGATAT    990
259   F  L  K  A  N  V  V  S  W  N  E  L  C  H  I  A  E  T  M  A  R  G  L  A  Y  L  H  E  D  I    288
```

FIG. 1B

| FIG. 2A |
|---|
| FIG. 2B |

FIG. 2

```
991  ACCTGGCTTAAAGATGGCCACAAGCCTGCAATCTCTCACAGGGACATCAAAAGTAAAAATGTGCTGTTGAAAACAATCTGACAGCTTG 1080
289   P  G  L  K  D  G  H  K  P  A  I  S  H  R  D  I  K  S  K  N  V  L  L  K  N  N  L  T  A  C   318
                                                                              _____
1081 CATTGCTGACTTTGGGCTTGGCCTTAAAGTTCGAGGCTGGCAAGTCTGCAGGTGACACCCATGGGCCAGGTTGGTACCCGGAGTATATGGC 1170
319   I  A  D  F  G  L  A  L  K  F  E  A  G  K  S  A  G  D  T  H  G  Q  V  G  T  R  R  Y  M  A   348

1171 TCCAGAGGTGTTGGAGGGTGCTATAAACTTCCAAAGGGACGCCATTTCTGAGGATAGATATGTACGCCCATGGATTAGTCCTATGGAATT 1260
349   P  E  V  L  E  G  A  I  N  F  Q  R  D  A  F  L  R  I  D  M  Y  A  M  G  L  V  L  W  E  L   378

1261 GGCTTCTCGTTGCACTGCTGCAGATGGACCCGTAGATGAGTACATGTTACCATTTGAGGAAGAAATTGGCCAGCATCCATTCTTGAAGA 1350
379   A  S  R  C  T  A  A  D  G  P  V  D  E  Y  M  L  P  F  E  E  E  I  G  Q  H  P  S  L  E  D   408

1351 TATGCAGGAAGTTGTTGTGCATAAAAAAGAGGCCTGTTTAAGAGATTATTGGCAGAAACATGCAGGAATGGCAATGCTCTGTGAAAC 1440
409   M  Q  E  V  V  V  H  K  K  K  R  P  V  L  R  D  Y  W  Q  K  H  A  G  M  A  M  L  C  E  T   438
                                                                          ↓
1441 GATAGAAGAATGTTGGGATCATGATGCAGAAGCCAGGTTATCAGCTGGATGTGTAGGTGAAAGAATTACTCAGATGCAAAGACTAACAA 1530
439   I  E  E  C  W  D  H  D  A  E  A  R  L  S  A  G  C  V  G  E  R  I  T  Q  M  Q  R  L  T  N   468
```

FIG. 2A

```
1531  TATCATTACTACAGAGGACATTGTAACAGTGGTCACAATGTTGACTTCCTCCCAAAGAATCTAGTCTATGATGGTGGCA  1620
 469   I  I  T  T  E  D  I  V  T  V  V  T  M  V  T  N  V  D  F  P  P  K  E  S  S  L  *          494

1621  CCGTCTGTACACACTGAGGACTGGACTCTGAACTGGAGCTGCTAAGGAAAGTGCTTAGTTGATTTTCTGTGTGAAATGAGTAGG  1710
1711  ATGCCTCCAGGACATGTACGCAAGCAGCCCCTTGTGGAAAGCATGGATCTGGGAGATGGAAACTTACTGCATCGTCTGCAGCA  1800
1801  CAGATATGAAGAGGAGTCTAAGGAGAAAGCTGCAAACTGTAAAGAACTTCTGAAAATGTACTGGCCCTCTCCAAATCAAG  1890
1891  GATCTTTGGACCTGGCTAATCAAGTATTGCAAAACTGACATCAGATTTCTTAATGTCTGCAGAAGACACTAATTCCTTAAATGAACT  1980
1981  ACTGCTATTTTTTAAATGAAAAACTTTCATTTCAGATTTTAAAAAGGTAACTTTTATTGCATTGCTGTTGTTTCTATAAATGAC  2070
2071  TATTGTAATGCCAACATGACACAGCTTGTGAATGTGTAGTGTGCTCTGTACATAGTCATCAAGTGGGTACAGTAAAGAGG  2160
2161  CTTCCAAGCATTACTTAACCTCCCTCAACAAGTTAATTACAAGTTAATTACAAGGTTGTTATTTAAGAAAAATGGTAAGCTATGCTTAGTGCCAATAG  2250
2251  AATAAATCAGTCCATGTTTATAAGCAGTGTTTAGCTTTTCTTCTACTGGCTTGTAATTAGGGAAAACAAGTGCTGTCTTTGAAATGGAAAAGA  2340
2341  TAAGTGGCTATTGTAAGCAGTGTTTAGCTTTTCTTCTACTGGCTGTAATTAGGGAAAACAAGTGCTGTCTTTGAAATGGAAAAGA  2430
2431  ATATGGTGTCACCCTACCCCCATACTTATCAAGGTCCCAAAATATTCTTTTTCCATTTCAAAGACACTTGAAACCCTAAATTA  2520
2521  CAAGCCAGTAGAGAAGAAAAGCTAAAACACGCTTTACAAATAGCC                                             2563
```

FIG. 2B tcgggaaaatgggagctgctgcaaagttggcgttcgcc gtctttcttatctcttgctc ttcaggtgctatacttggcagatcagaaactcaggagtgtcttttctttaatgctaattg ggaaagagacagaaccaaccagactggtgttgaaccttgctatggtgataaagataaacg gcgacattgttttgctacctggaagaatatttctggttccattgaaatagtgaagcaagg ttgttggctggatgatatcaactgctatgacaggactgattgtatagaaaaaaaagacag ccctgaagtgtacttttgttgctgtgagggcaatatgtgtaatgaaagttctcttattt tccggagatggaagtcacacagcccacttcaaatcctgttacaccgaagccaccctatta caacattctgctgtattccttggtaccactaatgttaattgcaggaattgtcatttgtgc atttggggtgtacagacatcacaagatggcctaccctcctgtacttgttcctactcaaca cgcctttcatataatgatagaggacccaggaccaccccacttccccattactagggtt gaagccattgcagctgttagaagtgaaagcaaggggaagatttggttgtgtctggaaagc ccagttgctcaatgaatatgtggctgtcaaaatatttccaatacaggacaaacagtcctg gcagaatgaatatgaagtctatagtctacctggaatgaagcatgagaacatactacagtt cattggtgcagagaaaagaggcaccagtgtggatgtggacctgtggctaatcacagcatt tcatgaaaagggctcactgtcagactttcttaaggctaatgtggtctcttggaatgaact ttgtcatattgcagaaaccatggctagaggattggcatatttacatgaggatatacctgg cttaaaagatggccacaagcctgcaatctctcacagggacatcaaaagtaaaaatgtgct gttgaaaaacaatctgacagcttgcattgctgactttgggttggccttaaagttcgaggc

FIG. 3

```
tggcaagtctgcaggtgacacccatgggcaggttggtacccggaggtatatggctccaga
ggtgttggagggtgctataaacttccaaagggacgcatttctgaggatagatatgtacgc
catgggattagtcctatgggaattggcttctcgttgcactgctgcagatggacccgtaga
tgagtacatgttaccatttgaggaagaaattggccagcatccatctcttgaagatatgca
ggaagttgttgtgcataaaaaaaagaggcctgttttaagagattattggcagaaacatgc
aggaatggcaatgctctgtgaaacgatagaagaatgtgggatcatgatgcagaagccag
gttatcagctggatgtgtaggtgaaagaattactcagatgcaaagactaacaaatatcat
tactacagaggacattgtaacagtggtcacaatggtgacaaatgttgactttcctcccaa
agaatctagtctatgatggtggcaccgtctgtacacactgaggactgggactctgaactg
gagctgctaagctaaggaaagtgcttagttgattttctgtgtgaaatgagtaggatgcct
ccaggacatgtacgcaagcagccccttgtggaaagcatggatctgggagatggatctggg
aaacttactgcatcgtctgcagcacagatatgaagaggagtctaagggaaaagctgcaaa
ctgtaaagaacttctgaaaatgtactcgaagaatgtggccctctccaaatcaaggatctt
ttggacctggctaatcaagtatttgcaaaactgacatcagatttcttaatgtctgtcaga
agacactaattccttaaatgaactactgctattttttttaaatgaaaaacttttcatttc
agattttaaaagggtaacttttttattgcatttgctgttgtttctataaatgactattgt
aatgccaacatgacacagcttgtgaatgtgtagtgtgctgctgttctgtgtacatagtca
tcaaagtggggtacagtaaagagg
```

FIG. 4

MetGlyAlaAlaAlaLysLeuAlaPheAlaValPheLeuIleSerCysSer
SerGlyAlaIleLeuGlyArgSerGluThrGlnGluCysLeuPhePheAsnAlaAsnTrp
GluArgAspArgThrAsnGlnThrGlyValGluProCysTyrGlyAspLysAspLysArg
ArgHisCysPheAlaThrTrpLysAsnIleSerGlySerIleGluIleValLysGlnGly
CysTrpLeuAspAspIleAsnCysTyrAspArgThrAspCysIleGluLysLysAspSer
ProGluValTyrPheCysCysCysGluGlyAsnMetCysAsnGluLysPheSerTyrPhe
ProGluMetGluValThrGlnProThrSerAsnProValThrProLysProProTyrTyr
AsnIleLeuLeuTyrSerLeuValProLeuMetLeuIleAlaGlyIleValIleCysAla
PheTrpValTyrArgHisHisLysMetAlaTyrProProValLeuValProThrGlnHis
AlaPheHisIleMetIleGluAspProGlyProProProProSerProLeuLeuGlyLeu
LysProLeuGlnLeuLeuGluValLysAlaArgGlyArgPheGlyCysValTrpLysAla
GlnLeuLeuAsnGluTyrValAlaValLysIlePheProIleGlnAspLysGlnSerTrp
GlnAsnGluTyrGluValTyrSerLeuProGlyMetLysHisGluAsnIleLeuGlnPhe
IleGlyAlaGluLysArgGlyThrSerValAspValAspLeuTrpLeuIleThrAlaPhe
HisGluLysGlySerLeuSerAspPheLeuLysAlaAsnValValSerTrpAsnGluLeu
CysHisIleAlaGluThrMetAlaArgGlyLeuAlaTyrLeuHisGluAspIleProGly
LeuLysAspGlyHisLysProAlaIleSerHisArgAspIleLysSerLysAsnValLeu
LeuLysAsnAsnLeuThrAlaCysIleAlaAspPheGlyLeuAlaLeuLysPheGluAla

FIG. 5

GlyLysSerAlaGlyAspThrHisGlyGlnValGlyThrArgArgTyrMetAlaProGlu

ValLeuGluGlyAlaIleAsnPheGlnArgAspAlaPheLeuArgIleAspMetTyrAla

MetGlyLeuValLeuTrpGluLeuAlaSerArgCysThrAlaAlaAspGlyProValAsp

GluTyrMetLeuProPheGluGluGluIleGlyGlnHisProSerLeuGluAspMetGln

GluValValValHisLysLysLysArgProValLeuArgAspTyrTrpGlnLysHisAla

GlyMetAlaMetLeuCysGluThrIleGluGluCysTrpAspHisAspAlaGluAlaArg

LeuSerAlaGlyCysValGlyGluArgIleThrGlnMetGlnArgLeuThrAsnIleIle

ThrThrGluAspIleValThrValValThrMetValThrAsnValAspPheProProLys

GluSerSerLeu***

| FIG. 8A |
| FIG. 8B |

GGACTTTCTGCTTTTCTGGG -181
ATAGATCCTAAAGGATTTCCATGGATATACATGCTTTATCTGGGATAAATCCTAGAAGCTCTCCATGGCACAAACTGTTTC -91
TCTCGGATTGCTTCTAAAATATCTAGGTCATTAAAAGGCTTTGTCATTGGATTGTTAGTAAAACACAAACCGAAAAGAAAAAAAC -1

ATGGGAGCTGCTACCAAGCTGGCCTTTGCAGTCTTTCTTATCTCCCTGTTCCTCAGCAGGATCGATCCTTGGAAGGTCGAAACCAAAGAA 90
 M  G  A  A  T  K  L  A  F  A  V  F  L  I  S  C  S  S  A  G  S  I  L  G  R  S  E  T  K  E

TGCCATCTACTACAATGCCAACTGGGAGAAGGACAAGACAAATTCCAACGGCACGGAGATCTGCTATGGGGATAATGATAAAGGAAGCAC 180
 C  I  Y  Y  N  A  N  W  E  K  D  K  T  N  S  N  G  T  E  I  C  Y  G  D  N  D  K  R  R  H

TGCTTTGCAACTTGGAAGAAACATTTCGGGCTCCATAGAAATTGTTAAGCAAGGCTGCTGGTTGGACGATATCAACTGCTATAACAAGAGC 270
 C  F  A  T  W  K  N  T  S  G  S  I  E  I  V  K  Q  G  C  W  L  D  D  I  N  C  Y  N  K  S

AAATGCACAGAGAAAAAGGATAGTCCAGATGTGTTTTTCTGTTGCTGCGAAGGAAAACTATTGCAATGAAAAGTTCTACCATTCACCAGAG 360
 K  C  T  E  K  K  D  S  P  D  V  F  F  C  C  C  E  G  N  Y  C  N  E  K  F  Y  H  S  P  E

FIG. 8A

```
ATGGAGGTCACACAGCCCCACCTCAAATCCTGTCACAACTAAGCCTCCTTTATTCAACACTCTGCTCTACTCACTGGTGCCTATCATGGTG      450
 M  E  V  T  Q  P  T  S  N  P  V  T  T  K  P  P  L  F  N  T  L  L  Y  S  L  V  P  I  M  V

GTTGCAGTGATTGTTCTCTTTCGTTTTGGATGTACCAAGCTCGCCTACCCCCCAGTGCTGGTTCCAACACAGGACCCAGGC                540
 V  A  V  I  V  L  F  S  F  W  M  Y  R  H  H  K  L  A  Y  P  P  V  L  V  P  T  Q  D  P  G

CCCCCTCCTCCGTCTCTGCTCTGGGATTAAAGCCGTTGCAGCTATTGGAGGTGAAAGCCAGAGGGAGGTTTGGCTGCGTGTGGAAAGCC       630
 P  P  P  S  P  L  L  G  L  K  P  L  Q  L  L  E  V  K  A  R  G  R  F  G  C  V  W  K  A

CAGTTATTAAATGAAACTGTAGCTGTCAAGATATTCCCTGTACAGGATAAACTGTCTTGGCAAAACGAGTATGAAATCTACAGCCTCCCT      720
 Q  L  L  N  E  T  V  A  V  K  I  F  P  V  Q  D  K  L  S  W  Q  N  E  Y  E  I  Y  S  L  P

GGGATGAAGCATGAGAATATCCTGTACTTCATTGGCGCCGAAAAACGTGGCACAAACCTTGACACAGATCTGTGGTTAATTACTGCTTTC     810
 G  M  K  H  E  N  I  L  Y  F  I  G  A  E  K  R  G  T  N  L  D  T  D  L  W  L  I  T  A  F

CACGAAAAGGGCTCCCTGACAGATTATCTCAAAGCCAACGTGGTGTCTTGGAATGAGCTTTGCCTCATCGCTGAGACAATGGCCAGAGGT    900
 H  E  K  G  S  L  T  D  Y  L  K  A  N  V  V  S  W  N  E  L  C  L  I  A  E  T  M  A  R  G

TTATCTCACCTCCATGAAGATATCCCAGGACTCAAAGATGGACACAAGCCTGCGGTAGCACATAGGGATATTAAAAGCAAAAATGTGCTA    990
 L  S  H  L  H  E  D  I  P  G  L  K  D  G  H  K  P  A  V  A  H  R  D  I  K  S  K  N  V  L
```

FIG. 8B

CTTAAAAACAATCTGACAGCCTGTATAGCAGACTTCGGCCTCGCCCTTAAAGTTCGAAGCTGGGAAATCTGCAGGGGACACACTCACGGGCAG 1080
L K N N L T A C I A D F G L A L K F E A G K S A G D T H G Q

GTTGGGACCCGCAGTACATGGCTCCAGAAGTGCTCGAGAAGTGTTAGAGAAGTGCTATCAATTTCCAGAGATGCCTTTTTAAGGATAGACATGTATGCG 1170
V G T R R Y M A P E V L E G A I N F Q R D A F L R I D M Y A

TTTGGTTTAGTACTTTGGGAGCTGGCATCAAGGTGCCACTGCCCTCAGATGGTCCTGTCGATGAGTATATGTTACCTTTTGAAGAAGAAGTT 1260
F G L V L W E L A S R C T A S D G P V D E Y M L P F E E E V

GGGCAGCAGACCCCATCTCTTGAGGACATGCAAGAAGTGGTAGTGCACAAAAAAGAAACCCATTTTAAGGGAGTGCTGCAGAAACATGCT 1350
G Q H P S L E D M Q E V V V H K K K R P I L R E C W Q K H A

GGAATGGCGATGCTCTGCGAAACCATAGAGGAGTGCTGGGATCACGACGCAGAGGCCAGGTTATCAGCCGGCTGCGTAGAAGAGCGAATC 1440
G M A M L C E T I E E C W D H D A E A R L S A G C V E E R I

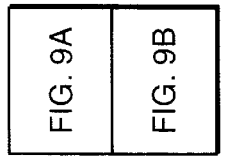

FIG. 9A

```
ATTCAAATGCAAAAACTCACAAACATTATCACCACCGAGGACACATTGTAACGATGGTGACAAACGTGACTTTCCGCCCAAG   1530
 I  Q  M  Q  K  L  T  N  I  I  T  T  E  D  I  V  T  V  V  T  M  V  T  N  V  D  F  P  P  K

GAATCAAGCCTATGATACCCTCAGTCATAACCGGACTCTGGTGCAGAGCTGCTAAGCTAAGGGAACTTCTGCCTAACAGCAGATACGGC   1620
 E  S  L
```

AAAGTCCACGTGAATCGAGGTGGGTTGCTCTCTTTGCAGATGGTCCCGTTGGACGACCGCCCTCTTCCAACTCGGAGACTTGTTTCATTC   1710
CATGCAAATGCCCAAAGGACGACTTGTTGCCGTTGCCTGCTTGGACAACAAAGGAATGAATGAAAGAAACAATGAAAGAAACACAAACCTC   1800
TCTCTAATAAACTGACACCTGTTTTTTTTTTTTTAAACACGTCAGAAAAGACTTATATCACGTGATCTACTGCTACTTTTTTTTTTT   1890
TAAATCAAAGCATTCATTTCAGATTTAAAGGTAACTGTTTTTATTGCCGTTGTGTTTCTCTCAATGACTATTGTAACGTCAT   1980
CATGACACAGCTTGTGAATGTTCCGTGTGCTGTGTCTGTATATAAAGCTAAAGTNATCAACGTGGGATATATTAAAGAGGCTTCC   2070
AAGCAGACTTTAACCNCCCTCAAAAAAAAAAAAAAAAAA

FIG. 9B

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

TACCCTCCTG TACTTGTTCC TACTCAA                             27

(2) INFORMATION FOR SEQ ID NO:2:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:2:

TAGCCACAGG TCCACATCCA CACTGGT                             27

(2) INFORMATION FOR SEQ ID NO:3:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:3:

CACGCCTTTC ATATAATGAT AGAG                                24

(2) INFORMATION FOR SEQ ID NO:4:

(i) SEQUENCE CHARACTERISTICS:
      (A) LENGTH: 2122 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: mouse (ix) FEATURE:
      (A) NAME/KEY: CDS
      (B) LOCATION: 9..1571

(xi) SEQUENCE DESCRIPTION: SEQ ID NO:4:

```
TCGGGAAA ATG GGA GCT GCT GCA AAG TTG GCG TTC GCC GTC TTT CTT ATC      50
         Met Gly Ala Ala Ala Lys Leu Ala Phe Ala Val Phe Leu Ile
           1               5                  10

TCT TGC TCT TCA GGT GCT ATA CTT GGC AGA TCA GAA ACT CAG GAG TGT       98
Ser Cys Ser Ser Gly Ala Ile Leu Gly Arg Ser Glu Thr Gln Glu Cys
 15              20                  25                  30
```

```
CTT TTC TTT AAT GCT AAT TGG GAA AGA GAC AGA ACC AAC CAG ACT GGT       146
Leu Phe Phe Asn Ala Asn Trp Glu Arg Asp Arg Thr Asn Gln Thr Gly
                35                  40                  45

GTT GAA CCT TGC TAT GGT GAT AAA GAT AAA CGG CGA CAT TGT TTT GCT       194
Val Glu Pro Cys Tyr Gly Asp Lys Asp Lys Arg Arg His Cys Phe Ala
            50                  55                  60

ACC TGG AAG AAT ATT TCT GGT TCC ATT GAA ATA GTG AAG CAA GGT TGT       242
Thr Trp Lys Asn Ile Ser Gly Ser Ile Glu Ile Val Lys Gln Gly Cys
        65                  70                  75

TGG CTG GAT GAT ATC AAC TGC TAT GAC AGG ACT GAT TGT ATA GAA AAA       290
Trp Leu Asp Asp Ile Asn Cys Tyr Asp Arg Thr Asp Cys Ile Glu Lys
    80                  85                  90

AAA GAC AGC CCT GAA GTG TAC TTT TGT TGC TGT GAG GGC AAT ATG TGT       338
Lys Asp Ser Pro Glu Val Tyr Phe Cys Cys Cys Glu Gly Asn Met Cys
95                  100                 105                 110

AAT GAA AAG TTC TCT TAT TTT CCG GAG ATG GAA GTC ACA CAG CCC ACT       386
Asn Glu Lys Phe Ser Tyr Phe Pro Glu Met Glu Val Thr Gln Pro Thr
                115                 120                 125

TCA AAT CCT GTT ACA CCG AAG CCA CCC TAT TAC AAC ATT CTG CTG TAT       434
Ser Asn Pro Val Thr Pro Lys Pro Pro Tyr Tyr Asn Ile Leu Leu Tyr
            130                 135                 140

TCC TTG GTA CCA CTA ATG TTA ATT GCA GGA ATT GTC ATT TGT GCA TTT       482
Ser Leu Val Pro Leu Met Leu Ile Ala Gly Ile Val Ile Cys Ala Phe
        145                 150                 155

TGG GTG TAC AGA CAT CAC AAG ATG GCC TAC CCT CCT GTA CTT GTT CCT       530
Trp Val Tyr Arg His His Lys Met Ala Tyr Pro Pro Val Leu Val Pro
    160                 165                 170

ACT CAA CAC GCC TTT CAT ATA ATG ATA GAG GAC CCA GGA CCA CCC CCA       578
Thr Gln His Ala Phe His Ile Met Ile Glu Asp Pro Gly Pro Pro Pro
175                 180                 185                 190

CCT TCC CCA TTA CTA GGG TTG AAG CCA TTG CAG CTG TTA GAA GTG AAA       626
Pro Ser Pro Leu Leu Gly Leu Lys Pro Leu Gln Leu Leu Glu Val Lys
                195                 200                 205

GCA AGG GGA AGA TTT GGT TGT GTC TGG AAA GCC CAG TTG CTC AAT GAA       674
Ala Arg Gly Arg Phe Gly Cys Val Trp Lys Ala Gln Leu Leu Asn Glu
            210                 215                 220

TAT GTG GCT GTC AAA ATA TTT CCA ATA CAG GAC AAA CAG TCC TGG CAG       722
Tyr Val Ala Val Lys Ile Phe Pro Ile Gln Asp Lys Gln Ser Trp Gln
        225                 230                 235

AAT GAA TAT GAA GTC TAT AGT CTA CCT GGA ATG AAG CAT GAG AAC ATA       770
Asn Glu Tyr Glu Val Tyr Ser Leu Pro Gly Met Lys His Glu Asn Ile
    240                 245                 250

CTA CAG TTC ATT GGT GCA GAG AAA AGA GGC ACC AGT GTG GAT GTG GAC       818
Leu Gln Phe Ile Gly Ala Glu Lys Arg Gly Thr Ser Val Asp Val Asp
255                 260                 265                 270

CTG TGG CTA ATC ACA GCA TTT CAT GAA AAG GGC TCA CTG TCA GAC TTT       866
Leu Trp Leu Ile Thr Ala Phe His Glu Lys Gly Ser Leu Ser Asp Phe
                275                 280                 285

CTT AAG GCT AAT GTG GTC TCT TGG AAT GAA CTT TGT CAT ATT GCA GAA       914
Leu Lys Ala Asn Val Val Ser Trp Asn Glu Leu Cys His Ile Ala Glu
            290                 295                 300

ACC ATG GCT AGA GGA TTG GCA TAT TTA CAT GAG GAT ATA CCT GGC TTA       962
Thr Met Ala Arg Gly Leu Ala Tyr Leu His Glu Asp Ile Pro Gly Leu
        305                 310                 315

AAA GAT GGC CAC AAG CCT GCA ATC TCT CAC AGG GAC ATC AAA AGT AAA      1010
Lys Asp Gly His Lys Pro Ala Ile Ser His Arg Asp Ile Lys Ser Lys
    320                 325                 330

AAT GTG CTG TTG AAA AAC AAT CTG ACA GCT TGC ATT GCT GAC TTT GGG      1058
Asn Val Leu Leu Lys Asn Asn Leu Thr Ala Cys Ile Ala Asp Phe Gly
```

```
             335                  340                  345                  350
TTG GCC TTA AAG TTC GAG GCT GGC AAG TCT GCA GGT GAC ACC CAT GGG                   1106
Leu Ala Leu Lys Phe Glu Ala Gly Lys Ser Ala Gly Asp Thr His Gly
                    355                  360                  365

CAG GTT GGT ACC CGG AGG TAT ATG GCT CCA GAG GTG TTG GAG GGT GCT                   1154
Gln Val Gly Thr Arg Arg Tyr Met Ala Pro Glu Val Leu Glu Gly Ala
            370                  375                  380

ATA AAC TTC CAA AGG GAC GCA TTT CTG AGG ATA GAT ATG TAC GCC ATG                   1202
Ile Asn Phe Gln Arg Asp Ala Phe Leu Arg Ile Asp Met Tyr Ala Met
                385                  390                  395

GGA TTA GTC CTA TGG GAA TTG GCT TCT CGT TGC ACT GCT GCA GAT GGA                   1250
Gly Leu Val Leu Trp Glu Leu Ala Ser Arg Cys Thr Ala Ala Asp Gly
            400                  405                  410

CCC GTA GAT GAG TAC ATG TTA CCA TTT GAG GAA GAA ATT GGC CAG CAT                   1298
Pro Val Asp Glu Tyr Met Leu Pro Phe Glu Glu Glu Ile Gly Gln His
415                  420                  425                  430

CCA TCT CTT GAA GAT ATG CAG GAA GTT GTT GTG CAT AAA AAA AAG AGG                   1346
Pro Ser Leu Glu Asp Met Gln Glu Val Val Val His Lys Lys Lys Arg
                435                  440                  445

CCT GTT TTA AGA GAT TAT TGG CAG AAA CAT GCA GGA ATG GCA ATG CTC                   1394
Pro Val Leu Arg Asp Tyr Trp Gln Lys His Ala Gly Met Ala Met Leu
            450                  455                  460

TGT GAA ACG ATA GAA GAA TGT TGG GAT CAT GAT GCA GAA GCC AGG TTA                   1442
Cys Glu Thr Ile Glu Glu Cys Trp Asp His Asp Ala Glu Ala Arg Leu
                465                  470                  475

TCA GCT GGA TGT GTA GGT GAA AGA ATT ACT CAG ATG CAA AGA CTA ACA                   1490
Ser Ala Gly Cys Val Gly Glu Arg Ile Thr Gln Met Gln Arg Leu Thr
            480                  485                  490

AAT ATC ATT ACT ACA GAG GAC ATT GTA ACA GTG GTC ACA ATG GTG ACA                   1538
Asn Ile Ile Thr Thr Glu Asp Ile Val Thr Val Val Thr Met Val Thr
495                  500                  505                  510

AAT GTT GAC TTT CCT CCC AAA GAA TCT AGT CTA TGATGGTGGC ACCGTCTGTA                 1591
Asn Val Asp Phe Pro Pro Lys Glu Ser Ser Leu
                515                  520

CACACTGAGG ACTGGGACTC TGAACTGGAG CTGCTAAGCT AAGGAAAGTG CTTAGTTGAT                 1651

TTTCTGTGTG AAATGAGTAG GATGCCTCCA GGACATGTAC GCAAGCAGCC CCTTGTGGAA                 1711

AGCATGGATC TGGGAGATGG ATCTGGGAAA CTTACTGCAT CGTCTGCAGC ACAGATATGA                 1771

AGAGGAGTCT AAGGGAAAAG CTGCAAACTG TAAAGAACTT CTGAAAATGT ACTCGAAGAA                 1831

TGTGGCCCTC TCCAAATCAA GGATCTTTTG GACCTGGCTA ATCAAGTATT TGCAAAACTG                 1891

ACATCAGATT TCTTAATGTC TGTCAGAAGA CACTAATTCC TTAAATGAAC TACTGCTATT                 1951

TTTTTTAAAT GAAAAACTTT TCATTTCAGA TTTTAAAAAG GGTAACTTTT TATTGCATTT                 2011

GCTGTTGTTT CTATAAATGA CTATTGTAAT GCCAACATGA CACAGCTTGT GAATGTGTAG                 2071

TGTGCTGCTG TTCTGTGTAC ATAGTCATCA AAGTGGGGTA CAGTAAAGAG G                         2122

(2) INFORMATION FOR SEQ ID NO:5:

(i) SEQUENCE CHARACTERISTICS:
          (A) LENGTH: 521 amino acids
          (B) TYPE: amino acid
          (D) TOPOLOGY: linear (ii) MOLECULE TYPE: protein (xi) SEQUENCE DESCRIPTION: SEQ ID NO:5:

Met Gly Ala Ala Ala Lys Leu Ala Phe Ala Val Phe Leu Ile Ser Cys
  1               5                  10                  15
```

```
Ser Ser Gly Ala Ile Leu Gly Arg Ser Glu Thr Gln Glu Cys Leu Phe
            20                  25                  30

Phe Asn Ala Asn Trp Glu Arg Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Ile Glu Lys Lys Asp
                85                  90                  95

Ser Pro Glu Val Tyr Phe Cys Cys Glu Gly Asn Met Cys Asn Glu
                100                 105                 110

Lys Phe Ser Tyr Phe Pro Glu Met Glu Val Thr Gln Pro Thr Ser Asn
            115                 120                 125

Pro Val Thr Pro Lys Pro Pro Tyr Tyr Asn Ile Leu Leu Tyr Ser Leu
        130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

His Ala Phe His Ile Met Ile Glu Asp Pro Gly Pro Pro Pro Pro Ser
            180                 185                 190

Pro Leu Leu Gly Leu Lys Pro Leu Gln Leu Leu Glu Val Lys Ala Arg
        195                 200                 205

Gly Arg Phe Gly Cys Val Trp Lys Ala Gln Leu Leu Asn Glu Tyr Val
    210                 215                 220

Ala Val Lys Ile Phe Pro Ile Gln Asp Lys Gln Ser Trp Gln Asn Glu
225                 230                 235                 240

Tyr Glu Val Tyr Ser Leu Pro Gly Met Lys His Glu Asn Ile Leu Gln
                245                 250                 255

Phe Ile Gly Ala Glu Lys Arg Gly Thr Ser Val Asp Val Asp Leu Trp
            260                 265                 270

Leu Ile Thr Ala Phe His Glu Lys Gly Ser Leu Ser Asp Phe Leu Lys
        275                 280                 285

Ala Asn Val Val Ser Trp Asn Glu Leu Cys His Ile Ala Glu Thr Met
290                 295                 300

Ala Arg Gly Leu Ala Tyr Leu His Glu Asp Ile Pro Gly Leu Lys Asp
305                 310                 315                 320

Gly His Lys Pro Ala Ile Ser His Arg Asp Ile Lys Ser Lys Asn Val
                325                 330                 335

Leu Leu Lys Asn Asn Leu Thr Ala Cys Ile Ala Asp Phe Gly Leu Ala
            340                 345                 350

Leu Lys Phe Glu Ala Gly Lys Ser Ala Gly Asp Thr His Gly Gln Val
        355                 360                 365

Gly Thr Arg Arg Tyr Met Ala Pro Glu Val Leu Glu Gly Ala Ile Asn
    370                 375                 380

Phe Gln Arg Asp Ala Phe Leu Arg Ile Asp Met Tyr Ala Met Gly Leu
385                 390                 395                 400

Val Leu Trp Glu Leu Ala Ser Arg Cys Thr Ala Ala Asp Gly Pro Val
                405                 410                 415

Asp Glu Tyr Met Leu Pro Phe Glu Glu Glu Ile Gly Gln His Pro Ser
            420                 425                 430

Leu Glu Asp Met Gln Glu Val Val Val His Lys Lys Lys Arg Pro Val
```

```
                      435                 440                 445
Leu Arg Asp Tyr Trp Gln Lys His Ala Gly Met Ala Met Leu Cys Glu
            450                 455                 460

Thr Ile Glu Glu Cys Trp Asp His Asp Ala Glu Ala Arg Leu Ser Ala
465                 470                 475                 480

Gly Cys Val Gly Glu Arg Ile Thr Gln Met Gln Arg Leu Thr Asn Ile
                485                 490                 495

Ile Thr Thr Glu Asp Ile Val Thr Val Val Thr Met Val Thr Asn Val
            500                 505                 510

Asp Phe Pro Pro Lys Glu Ser Ser Leu
            515                 520

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: frog (xi) SEQUENCE DESCRIPTION: SEQ ID NO:6:

CACGCCTTTC ACATTATGAT AGAG                                              24

(2) INFORMATION FOR SEQ ID NO:7:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

His Ala Phe His Ile Met Ile Glu
1               5

(2) INFORMATION FOR SEQ ID NO:8:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

TACCCTCCTG TACTTGTTCC TACTCAAGAC CCAGGACCAC CCCCACCTTC CCCATTACTA       60

GGGTTGAAGC CATTGCAGCT GTTAGAAGTG AAAGCAAGGG GAAGATTTGG TTGTGTCTGG      120

AAAGCCCAGT TGCTCAATGA ATATGTGGCT GTCAAAATAT TTCCAATACA GGACAAACAG      180

TCCTGGCAGA ATGAATATGA AGTCTATAGT CTACCTGGAA TGAAGCATGA GAACATACTA      240

CAGTTCATTG GTGCAGAGAA AAGAGGCACC AGTGTGGATG TGGACCTGTG GCTA            294

(2) INFORMATION FOR SEQ ID NO:9:

(i) SEQUENCE CHARACTERISTICS:
        (A) LENGTH: 19 base pairs
```

(B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:9:

TCGCCTACCC CCCAGTGCT                                            19

(2) INFORMATION FOR SEQ ID NO:10:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:10:

TCTGTGTCAA GGTTTGT                                              17

(2) INFORMATION FOR SEQ ID NO:11:

(i) SEQUENCE CHARACTERISTICS:
            (A) LENGTH: 1563 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: misc_feature
            (B) LOCATION: 1..3
            (D) OTHER INFORMATION: /product= "nnn represents ATG or
                hydrogen"

(xi) SEQUENCE DESCRIPTION: SEQ ID NO:11:

NNNGGAGCTG CTGCAAAGTT GGCGTTCGCC GTCTTTCTTA TCTCTTGCTC TTCAGGTGCT    60

ATACTTGGCA GATCAGAAAC TCAGGAGTGT CTTTTCTTTA ATGCTAATTG GGAAAGAGAC   120

AGAACCAACC AGACTGGTGT TGAACCTTGC TATGGTGATA AGATAAACG GCGACATTGT    180

TTTGCTACCT GGAAGAATAT TTCTGGTTCC ATTGAAATAG TGAAGCAAGG TTGTTGGCTG   240

GATGATATCA ACTGCTATGA CAGGACTGAT TGTATAGAAA AAAAGACAG CCCTGAAGTG    300

TACTTTTGTT GCTGTGAGGG CAATATGTGT AATGAAAAGT TCTCTTATTT TCCGGAGATG   360

GAAGTCACAC AGCCCACTTC AAATCCTGTT ACACCGAAGC CACCCTATTA CAACATTCTG   420

CTGTATTCCT TGGTACCACT AATGTTAATT GCAGGAATTG TCATTTGTGC ATTTTGGGTG   480

TACAGACATC ACAAGATGGC CTACCCTCCT GTACTTGTTC CTACTCAACA CGCCTTTCAT   540

ATAATGATAG AGGACCCAGG ACCACCCCCA CCTTCCCCAT TACTAGGGTT GAAGCCATTG   600

CAGCTGTTAG AAGTGAAAGC AAGGGGAAGA TTTGGTTGTG TCTGGAAAGC CCAGTTGCTC   660

AATGAATATG TGGCTGTCAA AATATTTCCA ATACAGGACA AACAGTCCTG GCAGAATGAA   720

TATGAAGTCT ATAGTCTACC TGGAATGAAG CATGAGAACA TACTACAGTT CATTGGTGCA   780

GAGAAAAGAG GCACCAGTGT GGATGTGGAC CTGTGGCTAA TCACAGCATT TCATGAAAAG   840

GGCTCACTGT CAGACTTTCT TAAGGCTAAT GTGGTCTCTT GGAATGAACT TTGTCATATT   900

GCAGAAACCA TGGCTAGAGG ATTGGCATAT TTACATGAGG ATATACCTGG CTTAAAAGAT   960

GGCCACAAGC CTGCAATCTC TCACAGGGAC ATCAAAAGTA AAAATGTGCT GTTGAAAAAC  1020

AATCTGACAG CTTGCATTGC TGACTTTGGG TTGGCCTTAA AGTTCGAGGC TGGCAAGTCT  1080

```
GCAGGTGACA CCCATGGGCA GGTTGGTACC CGGAGGTATA TGGCTCCAGA GGTGTTGGAG    1140

GGTGCTATAA ACTTCCAAAG GGACGCATTT CTGAGGATGA ATATGTACGC CATGGGATTA    1200

GTCCTATGGG AATTGGCTTC TCGTTGCACT GCTGCAGATG GACCCGTAGA TGAGTACATG    1260

TTACCATTTG AGGAAGAAAT TGGCCAGCAT CCATCTCTTG AAGATATGCA GGAAGTTGTT    1320

GTGCATAAAA AAAGAGGCC TGTTTTAAGA GATTATTGGC AGAAACATGC AGGAATGGCA     1380

ATGCTCTGTG AAACGATAGA AGAATGTTGG GATCATGATG CAGAAGCCAG GTTATCAGCT    1440

GGATGTGTAG GTGAAAGAAT TACTCAGATG CAAAGACTAA CAAATATCAT TACTACAGAG    1500

GACATTGTAA CAGTGGTCAC AATGGTGACA AATGTTGACT TTCCTCCCAA AGAATCTAGT    1560

CTA                                                                  1563

(2) INFORMATION FOR SEQ ID NO:12:

(i) SEQUENCE CHARACTERISTICS:
        (A) LENGTH: 2563 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: mouse (ix) FEATURE:
        (A) NAME/KEY: CDS
        (B) LOCATION: 71..1609

(ix) FEATURE:
        (A) NAME/KEY: sig_peptide
        (B) LOCATION: 71..127

(ix) FEATURE:
        (A) NAME/KEY: mat_peptide
        (B) LOCATION: 128..1609

(xi) SEQUENCE DESCRIPTION: SEQ ID NO:12:

CTCCGAGGAA GACCCAGGGA ACTGGATATC TAGCGAGAAC TTCCTACGGC TTCTCCGGCG     60

CCTCGGGAAA ATG GGA GCT GCT GCA AAG TTG GCG TTC GCC GTC TTT CTT      109
             Met Gly Ala Ala Ala Lys Leu Ala Phe Ala Val Phe Leu
             -19             -15                 -10

ATC TCT TGC TCT TCA GGT GCT ATA CTT GGC AGA TCA GAA ACT CAG GAG      157
Ile Ser Cys Ser Ser Gly Ala Ile Leu Gly Arg Ser Glu Thr Gln Glu
    -5                1               5                   10

TGT CTT TTC TTT AAT GCT AAT TGG GAA AGA GAC AGA ACC AAC CAG ACT      205
Cys Leu Phe Phe Asn Ala Asn Trp Glu Arg Asp Arg Thr Asn Gln Thr
                 15                  20                  25

GGT GTT GAA CCT TGC TAT GGT GAT AAA GAT AAA CGG CGA CAT TGT TTT      253
Gly Val Glu Pro Cys Tyr Gly Asp Lys Asp Lys Arg Arg His Cys Phe
             30                  35                  40

GCT ACC TGG AAG AAT ATT TCT GGT TCC ATT GAA ATA GTG AAG CAA GGT      301
Ala Thr Trp Lys Asn Ile Ser Gly Ser Ile Glu Ile Val Lys Gln Gly
             45                  50                  55

TGT TGG CTG GAT GAT ATC AAC TGC TAT GAC AGG ACT GAT TGT ATA GAA      349
Cys Trp Leu Asp Asp Ile Asn Cys Tyr Asp Arg Thr Asp Cys Ile Glu
        60                  65                  70

AAA AAA GAC AGC CCT GAA GTG TAC TTT TGT TGC TGT GAG GGC AAT ATG      397
Lys Lys Asp Ser Pro Glu Val Tyr Phe Cys Cys Cys Glu Gly Asn Met
    75                  80                  85                  90

TGT AAT GAA AAG TTC TCT TAT TTT CCG GAG ATG GAA GTC ACA CAG CCC      445
Cys Asn Glu Lys Phe Ser Tyr Phe Pro Glu Met Glu Val Thr Gln Pro
```

```
                        95                    100                      105
ACT TCA AAT CCT GTT ACA CCG AAG CCA CCC TAT TAC AAC ATT CTG CTG         493
Thr Ser Asn Pro Val Thr Pro Lys Pro Pro Tyr Tyr Asn Ile Leu Leu
            110                 115                 120

TAT TCC TTG GTA CCA CTA ATG TTA ATT GCA GGA ATT GTC ATT TGT GCA         541
Tyr Ser Leu Val Pro Leu Met Leu Ile Ala Gly Ile Val Ile Cys Ala
            125                 130                 135

TTT TGG GTG TAC AGA CAT CAC AAG ATG GCC TAC CCT CCT GTA CTT GTT         589
Phe Trp Val Tyr Arg His His Lys Met Ala Tyr Pro Pro Val Leu Val
            140                 145                 150

CCT ACT CAA GAC CCA GGA CCA CCC CCA CCT TCC CCA TTA CTA GGG TTG         637
Pro Thr Gln Asp Pro Gly Pro Pro Pro Pro Ser Pro Leu Leu Gly Leu
155             160                 165                 170

AAG CCA TTG CAG CTG TTA GAA GTG AAA GCA AGG GGA AGA TTT GGT TGT         685
Lys Pro Leu Gln Leu Leu Glu Val Lys Ala Arg Gly Arg Phe Gly Cys
            175                 180                 185

GTC TGG AAA GCC CAG TTG CTC AAT GAA TAT GTG GCT GTC AAA ATA TTT         733
Val Trp Lys Ala Gln Leu Leu Asn Glu Tyr Val Ala Val Lys Ile Phe
            190                 195                 200

CCA ATA CAG GAC AAA CAG TCC TGG CAG AAT GAA TAT GAA GTC TAT AGT         781
Pro Ile Gln Asp Lys Gln Ser Trp Gln Asn Glu Tyr Glu Val Tyr Ser
            205                 210                 215

CTA CCT GGA ATG AAG CAT GAG AAC ATA CTA CAG TTC ATT GGT GCA GAG         829
Leu Pro Gly Met Lys His Glu Asn Ile Leu Gln Phe Ile Gly Ala Glu
            220                 225                 230

AAA AGA GGC ACC AGT GTG GAT GTG GAC CTG TGG CTA ATC ACA GCA TTT         877
Lys Arg Gly Thr Ser Val Asp Val Asp Leu Trp Leu Ile Thr Ala Phe
235             240                 245                 250

CAT GAA AAG GGC TCA CTG TCA GAC TTT CTT AAG GCT AAT GTG GTC TCT         925
His Glu Lys Gly Ser Leu Ser Asp Phe Leu Lys Ala Asn Val Val Ser
            255                 260                 265

TGG AAT GAA CTT TGT CAT ATT GCA GAA ACC ATG GCT AGA GGA TTG GCA         973
Trp Asn Glu Leu Cys His Ile Ala Glu Thr Met Ala Arg Gly Leu Ala
            270                 275                 280

TAT TTA CAT GAG GAT ATA CCT GGC TTA AAA GAT GGC CAC AAG CCT GCA        1021
Tyr Leu His Glu Asp Ile Pro Gly Leu Lys Asp Gly His Lys Pro Ala
            285                 290                 295

ATC TCT CAC AGG GAC ATC AAA AGT AAA AAT GTG CTG TTG AAA AAC AAT        1069
Ile Ser His Arg Asp Ile Lys Ser Lys Asn Val Leu Leu Lys Asn Asn
300             305                 310

CTG ACA GCT TGC ATT GCT GAC TTT GGG TTG GCC TTA AAG TTC GAG GCT        1117
Leu Thr Ala Cys Ile Ala Asp Phe Gly Leu Ala Leu Lys Phe Glu Ala
315             320                 325                 330

GGC AAG TCT GCA GGT GAC ACC CAT GGG CAG GTT GGT ACC CGG AGG TAT        1165
Gly Lys Ser Ala Gly Asp Thr His Gly Gln Val Gly Thr Arg Arg Tyr
            335                 340                 345

ATG GCT CCA GAG GTG TTG GAG GGT GCT ATA AAC TTC CAA AGG GAC GCA        1213
Met Ala Pro Glu Val Leu Glu Gly Ala Ile Asn Phe Gln Arg Asp Ala
            350                 355                 360

TTT CTG AGG ATA GAT ATG TAC GCC ATG GGA TTA GTC CTA TGG GAA TTG        1261
Phe Leu Arg Ile Asp Met Tyr Ala Met Gly Leu Val Leu Trp Glu Leu
            365                 370                 375

GCT TCT CGT TGC ACT GCT GCA GAT GGA CCC GTA GAT GAG TAC ATG TTA        1309
Ala Ser Arg Cys Thr Ala Ala Asp Gly Pro Val Asp Glu Tyr Met Leu
            380                 385                 390

CCA TTT GAG GAA GAA ATT GGC CAG CAT CCA TCT CTT GAA GAT ATG CAG        1357
Pro Phe Glu Glu Glu Ile Gly Gln His Pro Ser Leu Glu Asp Met Gln
395             400                 405                 410

GAA GTT GTT GTG CAT AAA AAA AAG AGG CCT GTT TTA AGA GAT TAT TGG        1405
```

```
        Glu Val Val His Lys Lys Arg Pro Val Leu Arg Asp Tyr Trp
                    415                 420                 425

CAG AAA CAT GCA GGA ATG GCA ATG CTC TGT GAA ACG ATA GAA GAA TGT            1453
Gln Lys His Ala Gly Met Ala Met Leu Cys Glu Thr Ile Glu Glu Cys
                430                 435                 440

TGG GAT CAT GAT GCA GAA GCC AGG TTA TCA GCT GGA TGT GTA GGT GAA            1501
Trp Asp His Asp Ala Glu Ala Arg Leu Ser Ala Gly Cys Val Gly Glu
                445                 450                 455

AGA ATT ACT CAG ATG CAA AGA CTA ACA AAT ATC ATT ACT ACA GAG GAC            1549
Arg Ile Thr Gln Met Gln Arg Leu Thr Asn Ile Ile Thr Thr Glu Asp
        460                 465                 470

ATT GTA ACA GTG GTC ACA ATG GTG ACA AAT GTT GAC TTT CCT CCC AAA            1597
Ile Val Thr Val Val Thr Met Val Thr Asn Val Asp Phe Pro Pro Lys
475                 480                 485                 490

GAA TCT AGT CTA TGATGGTGGC ACCGTCTGTA CACACTGAGG ACTGGGACTC                1649
Glu Ser Ser Leu

TGAACTGGAG CTGCTAAGCT AAGGAAAGTG CTTAGTTGAT TTTCTGTGTG AAATGAGTAG          1709

GATGCCTCCA GGACATGTAC GCAAGCAGCC CCTTGTGGAA AGCATGGATC TGGGAGATGG          1769

ATCTGGGAAA CTTACTGCAT CGTCTGCAGC ACAGATATGA AGAGGAGTCT AAGGGAAAAG          1829

CTGCAAACTG TAAAGAACTT CTGAAAATGT ACTCGAAGAA TGTGGCCCTC TCCAAATCAA          1889

GGATCTTTTG GACCTGGCTA ATCAAGTATT TGCAAAACTG ACATCAGATT TCTTAATGTC          1949

TGTCAGAAGA CACTAATTCC TTAAATGAAC TACTGCTATT TTTTTAAAT GAAAACTTT            2009

TCATTTCAGA TTTTAAAAAG GGTAACTTTT TATTGCATTT GCTGTTGTTT CTATAAATGA          2069

CTATTGTAAT GCCAACATGA CACAGCTTGT GAATGTGTAG TGTGCTGCTG TTCTGTGTAC          2129

ATAGTCATCA AAGTGGGGTA CAGTAAAGAG GCTTCCAAGC ATTACTTTAA CCTCCCTCAA          2189

CAAGGTATAC CTCAGTTCCA CGGTTGTTAA ATTATAAAAT TGAAAACACT AACAGAATTT          2249

GAATAAATCA GTCCATGTTT TATAACAAGG TTAATTACAA ATTCACTGTG TTATTTAAGA          2309

AAAAATGGTA AGCTATGCTT AGTGCCAATA GTAAGTGGCT ATTTGTAAAG CAGTGTTTTA          2369

GCTTTTCTTC TACTGGCTTG TAATTTAGGG AAAACAAGTG CTGTCTTTGA AATGGAAAAG          2429

AATATGGTGT CACCCTACCC CCCATACTTA TATCAAGGTC CCAAAATATT CTTTTCCATT          2489

TCAAAGACAG CACTTTGAAA ACCCTAAATT ACAAGCCAGT AGAAGAAAAG CTAAAACACG          2549

CTTTACAAAT AGCC                                                            2563

(2) INFORMATION FOR SEQ ID NO:13:

(i) SEQUENCE CHARACTERISTICS:
        (A) LENGTH: 513 amino acids
        (B) TYPE: amino acid
        (D) TOPOLOGY: linear (ii) MOLECULE TYPE: protein (xi) SEQUENCE DESCRIPTION: SEQ ID NO:13:

Met Gly Ala Ala Ala Lys Leu Ala Phe Ala Val Phe Leu Ile Ser Cys
-19             -15                 -10                 -5

Ser Ser Gly Ala Ile Leu Gly Arg Ser Glu Thr Gln Glu Cys Leu Phe
            1               5                   10

Phe Asn Ala Asn Trp Glu Arg Asp Arg Thr Asn Gln Thr Gly Val Glu
        15                  20                  25

Pro Cys Tyr Gly Asp Lys Asp Lys Arg His Cys Phe Ala Thr Trp
    30                  35                  40                  45

Lys Asn Ile Ser Gly Ser Ile Glu Ile Val Lys Gln Gly Cys Trp Leu
```

```
                      50                  55                  60
Asp Asp Ile Asn Cys Tyr Asp Arg Thr Asp Cys Ile Glu Lys Lys Asp
                65                  70                  75
Ser Pro Glu Val Tyr Phe Cys Cys Glu Gly Asn Met Cys Asn Glu
            80                  85                  90
Lys Phe Ser Tyr Phe Pro Glu Met Glu Val Thr Gln Pro Thr Ser Asn
        95                  100                 105
Pro Val Thr Pro Lys Pro Pro Tyr Tyr Asn Ile Leu Leu Tyr Ser Leu
110                 115                 120                 125
Val Pro Leu Met Leu Ile Ala Gly Ile Val Ile Cys Ala Phe Trp Val
                130                 135                 140
Tyr Arg His His Lys Met Ala Tyr Pro Pro Val Leu Val Pro Thr Gln
                145                 150                 155
Asp Pro Gly Pro Pro Pro Pro Ser Pro Leu Leu Gly Leu Lys Pro Leu
                160                 165                 170
Gln Leu Leu Glu Val Lys Ala Arg Gly Arg Phe Gly Cys Val Trp Lys
            175                 180                 185
Ala Gln Leu Leu Asn Glu Tyr Val Ala Val Lys Ile Phe Pro Ile Gln
190                 195                 200                 205
Asp Lys Gln Ser Trp Gln Asn Glu Tyr Glu Val Tyr Ser Leu Pro Gly
                210                 215                 220
Met Lys His Glu Asn Ile Leu Gln Phe Ile Gly Ala Glu Lys Arg Gly
                225                 230                 235
Thr Ser Val Asp Val Asp Leu Trp Leu Ile Thr Ala Phe His Glu Lys
            240                 245                 250
Gly Ser Leu Ser Asp Phe Leu Lys Ala Asn Val Val Ser Trp Asn Glu
            255                 260                 265
Leu Cys His Ile Ala Glu Thr Met Ala Arg Gly Leu Ala Tyr Leu His
270                 275                 280                 285
Glu Asp Ile Pro Gly Leu Lys Asp Gly His Lys Pro Ala Ile Ser His
                290                 295                 300
Arg Asp Ile Lys Ser Lys Asn Val Leu Leu Lys Asn Asn Leu Thr Ala
                305                 310                 315
Cys Ile Ala Asp Phe Gly Leu Ala Leu Lys Phe Glu Ala Gly Lys Ser
            320                 325                 330
Ala Gly Asp Thr His Gly Gln Val Gly Thr Arg Arg Tyr Met Ala Pro
335                 340                 345
Glu Val Leu Glu Gly Ala Ile Asn Phe Gln Arg Asp Ala Phe Leu Arg
350                 355                 360                 365
Ile Asp Met Tyr Ala Met Gly Leu Val Leu Trp Glu Leu Ala Ser Arg
                370                 375                 380
Cys Thr Ala Ala Asp Gly Pro Val Asp Glu Tyr Met Leu Pro Phe Glu
            385                 390                 395
Glu Glu Ile Gly Gln His Pro Ser Leu Glu Asp Met Gln Glu Val Val
            400                 405                 410
Val His Lys Lys Lys Arg Pro Val Leu Arg Asp Tyr Trp Gln Lys His
            415                 420                 425
Ala Gly Met Ala Met Leu Cys Glu Thr Ile Glu Glu Cys Trp Asp His
430                 435                 440                 445
Asp Ala Glu Ala Arg Leu Ser Ala Gly Cys Val Gly Glu Arg Ile Thr
                450                 455                 460
Gln Met Gln Arg Leu Thr Asn Ile Ile Thr Thr Glu Asp Ile Val Thr
                465                 470                 475
```

```
Val Val Thr Met Val Thr Asn Val Asp Phe Pro Pro Lys Glu Ser Ser
        480                 485                 490
Leu (2) INFORMATION FOR SEQ ID NO:14:

(i) SEQUENCE CHARACTERISTICS:
        (A) LENGTH: 2313 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: frog (ix) FEATURE:
        (A) NAME/KEY: CDS
        (B) LOCATION: 202..1743

(xi) SEQUENCE DESCRIPTION: SEQ ID NO:14:

GGACTTTCTG CTTTTTCTGG GATAGATCCT AAAGGATTTC CATGGATATA CATGCATATT      60

GCTTTATCTG GGATAAATCC TAGAAGCTCT CCATGGGCAC AAACTGTTTT CTCTCGGATT     120

GCTTCTAAAA TATCTAGGTC ATTAAAGGCT TTGTCATTGG ATTGTTAGTA AAAAGGAACA     180

CAAACCGAAA AGGAAAAAAA C ATG GGA GCT GCT ACC AAG CTG GCC TTT GCA      231
                        Met Gly Ala Ala Thr Lys Leu Ala Phe Ala
                         1               5                  10

GTC TTT CTT ATC TCC TGT TCC TCA GCA GGA TCG ATC CTT GGA AGG TCG      279
Val Phe Leu Ile Ser Cys Ser Ser Ala Gly Ser Ile Leu Gly Arg Ser
             15                  20                  25

GAA ACC AAA GAA TGC ATC TAC TAC AAT GCC AAC TGG GAG AAG GAC AAG      327
Glu Thr Lys Glu Cys Ile Tyr Tyr Asn Ala Asn Trp Glu Lys Asp Lys
         30                  35                  40

ACA AAT TCC AAC GGC ACG GAG ATC TGC TAT GGG GAT AAT GAT AAA AGG      375
Thr Asn Ser Asn Gly Thr Glu Ile Cys Tyr Gly Asp Asn Asp Lys Arg
     45                  50                  55

AAG CAC TGC TTT GCA ACT TGG AAG AAC ATT TCG GGC TCC ATA GAA ATT      423
Lys His Cys Phe Ala Thr Trp Lys Asn Ile Ser Gly Ser Ile Glu Ile
 60                  65                  70

GTT AAG CAA GGC TGC TGG TTG GAC GAT ATC AAC TGC TAT AAC AAG AGC      471
Val Lys Gln Gly Cys Trp Leu Asp Asp Ile Asn Cys Tyr Asn Lys Ser
 75                  80                  85                  90

AAA TGC ACA GAG AAA AAG GAT AGT CCA GAT GTG TTT TTC TGT TGC TGC      519
Lys Cys Thr Glu Lys Lys Asp Ser Pro Asp Val Phe Phe Cys Cys Cys
                 95                 100                 105

GAA GGA AAC TAT TGC AAT GAA AAG TTC TAC CAT TCA CCA GAG ATG GAG      567
Glu Gly Asn Tyr Cys Asn Glu Lys Phe Tyr His Ser Pro Glu Met Glu
             110                 115                 120

GTC ACA CAG CCC ACC TCA AAT CCT GTC ACA ACT AAG CCT CCT TTA TTC      615
Val Thr Gln Pro Thr Ser Asn Pro Val Thr Thr Lys Pro Pro Leu Phe
         125                 130                 135

AAC ACT CTG CTC TAC TCA CTG GTG CCT ATC ATG GTG GTT GCA GTG ATT      663
Asn Thr Leu Leu Tyr Ser Leu Val Pro Ile Met Val Val Ala Val Ile
     140                 145                 150

GTT CTC TTC TCG TTT TGG ATG TAC CGA CAT CAC AAG CTC GCC TAC CCC      711
Val Leu Phe Ser Phe Trp Met Tyr Arg His His Lys Leu Ala Tyr Pro
155                 160                 165                 170

CCA GTG CTG GTT CCA ACA CAG GAC CCA GGC CCC CCT CCT CCG TCT CCT      759
Pro Val Leu Val Pro Thr Gln Asp Pro Gly Pro Pro Pro Pro Ser Pro
                 175                 180                 185
```

```
CTG CTG GGA TTA AAG CCG TTG CAG CTA TTG GAG GTG AAA GCC AGA GGG       807
Leu Leu Gly Leu Lys Pro Leu Gln Leu Leu Glu Val Lys Ala Arg Gly
            190                 195                 200

AGG TTT GGC TGC GTG TGG AAA GCC CAG TTA TTA AAT GAA ACT GTA GCT       855
Arg Phe Gly Cys Val Trp Lys Ala Gln Leu Leu Asn Glu Thr Val Ala
            205                 210                 215

GTC AAG ATA TTC CCT GTA CAG GAT AAA CTG TCT TGG CAA AAC GAG TAT       903
Val Lys Ile Phe Pro Val Gln Asp Lys Leu Ser Trp Gln Asn Glu Tyr
            220                 225                 230

GAA ATC TAC AGC CTC CCT GGG ATG AAG CAT GAG AAT ATC CTG TAC TTC       951
Glu Ile Tyr Ser Leu Pro Gly Met Lys His Glu Asn Ile Leu Tyr Phe
235                 240                 245                 250

ATT GGC GCC GAA AAA CGT GGC ACA AAC CTT GAC ACA GAT CTG TGG TTA       999
Ile Gly Ala Glu Lys Arg Gly Thr Asn Leu Asp Thr Asp Leu Trp Leu
            255                 260                 265

ATT ACT GCT TTC CAC GAA AAG GGC TCC CTG ACA GAC TAT CTC AAA GCC      1047
Ile Thr Ala Phe His Glu Lys Gly Ser Leu Thr Asp Tyr Leu Lys Ala
            270                 275                 280

AAC GTG GTG TCT TGG AAT GAG CTT TGC CTC ATC GCT GAG ACA ATG GCC      1095
Asn Val Val Ser Trp Asn Glu Leu Cys Leu Ile Ala Glu Thr Met Ala
            285                 290                 295

AGA GGT TTA TCT CAC CTC CAT GAA GAT ATC CCA GGA CTC AAA GAT GGA      1143
Arg Gly Leu Ser His Leu His Glu Asp Ile Pro Gly Leu Lys Asp Gly
300                 305                 310

CAC AAG CCT GCG GTA GCA CAT AGG GAT ATT AAA AGC AAA AAT GTG CTA      1191
His Lys Pro Ala Val Ala His Arg Asp Ile Lys Ser Lys Asn Val Leu
315                 320                 325                 330

CTT AAA AAC AAT CTG ACA GCC TGT ATA GCA GAC TTC GGC CTC GCC TTA      1239
Leu Lys Asn Asn Leu Thr Ala Cys Ile Ala Asp Phe Gly Leu Ala Leu
            335                 340                 345

AAG TTC GAA GCT GGG AAA TCT GCA GGG GAC ACT CAC GGG CAG GTT GGG      1287
Lys Phe Glu Ala Gly Lys Ser Ala Gly Asp Thr His Gly Gln Val Gly
            350                 355                 360

ACC CGC AGG TAC ATG GCT CCA GAA GTG TTA GAA GGT GCT ATC AAT TTC      1335
Thr Arg Arg Tyr Met Ala Pro Glu Val Leu Glu Gly Ala Ile Asn Phe
            365                 370                 375

CAG AGA GAT GCC TTT TTA AGG ATA GAC ATG TAT GCG TTT GGT TTA GTA      1383
Gln Arg Asp Ala Phe Leu Arg Ile Asp Met Tyr Ala Phe Gly Leu Val
            380                 385                 390

CTT TGG GAG CTG GCA TCA AGG TGC ACT GCC TCA GAT GGT CCT GTC GAT      1431
Leu Trp Glu Leu Ala Ser Arg Cys Thr Ala Ser Asp Gly Pro Val Asp
395                 400                 405                 410

GAG TAT ATG TTA CCT TTT GAA GAA GAA GTT GGG CAG CAC CCA TCT CTT      1479
Glu Tyr Met Leu Pro Phe Glu Glu Glu Val Gly Gln His Pro Ser Leu
            415                 420                 425

GAG GAC ATG CAA GAA GTG GTA GTG CAC AAA AAG AAA AGA CCC ATT TTA      1527
Glu Asp Met Gln Glu Val Val Val His Lys Lys Lys Arg Pro Ile Leu
            430                 435                 440

AGG GAG TGC TGG CAG AAA CAT GCT GGA ATG GCG ATG CTC TGC GAA ACC      1575
Arg Glu Cys Trp Gln Lys His Ala Gly Met Ala Met Leu Cys Glu Thr
            445                 450                 455

ATA GAG GAG TGC TGG GAT CAC GAC GCA GAG GCC AGG TTA TCA GCC GGC      1623
Ile Glu Glu Cys Trp Asp His Asp Ala Glu Ala Arg Leu Ser Ala Gly
            460                 465                 470

TGC GTA GAA GAG CGA ATC ATT CAA ATG CAA AAA CTC ACA AAC ATT ATC      1671
Cys Val Glu Glu Arg Ile Ile Gln Met Gln Lys Leu Thr Asn Ile Ile
475                 480                 485                 490

ACC ACC GAG GAC ATT GTA ACA GTC GTA ACG ATG GTG ACA AAC GTG GAC      1719
Thr Thr Glu Asp Ile Val Thr Val Val Thr Met Val Thr Asn Val Asp
```

```
                    495               500             505
TTT CCG CCC AAG GAA TCA AGC CTA TGATACCCTC AGTCATAACC GGACTCTGGT    1773
Phe Pro Pro Lys Glu Ser Ser Leu
            510

GCAGAGCTGC TAAGCTAAGG GGAACTTCTG CCTAACAGCA GATACGGCAA AGTCCACGTG    1833

AATCGAGGTG GGTTGCTCTT TTGCAGATGG TCCCGTTTGG ACGACCCGCC TCTTCCAACT    1893

CGGAGACTTG TTTCATTCCA TGCAAATGCC CAAAGGACTT GTTGACTTGC CGTGGTTTTT    1953

ATTGGACAAC AAAGGAATGA AGAAAACAA TGAAGAAACA CAAACCTCTC TCTAATAAAC    2013

TGACACCTGT TTTTTTTTTT TTTAAACACG TCAGAAAAGA CTTATATCAC GTGATCTACT    2073

GCTACTTTTT TTTTTTTTTA AATCAAAGCA TTTCATTTCA GATTTAAAGG GTAACTGTTT    2133

TTATTGCATT TGCCGTTGTG TTTCTCTCAA TGACTATTGT AACGTCATCA TGACACAGCT    2193

TGTGAATGTT CCGTGTGCTG CTGTTCTGTG TATATAAAAG CTAAAGTATC AACGTGGGAT    2253

ATATTAAAGA GGCTTCCAAG CAGACTTTAA CCCCCTCAAA AAAAAAAAAA AAAAAAAAA    2313

(2) INFORMATION FOR SEQ ID NO:15:

(i) SEQUENCE CHARACTERISTICS:
        (A) LENGTH: 514 amino acids
        (B) TYPE: amino acid
        (D) TOPOLOGY: linear (ii) MOLECULE TYPE: protein (xi) SEQUENCE DESCRIPTION: SEQ ID NO:15:

Met Gly Ala Ala Thr Lys Leu Ala Phe Ala Val Phe Leu Ile Ser Cys
 1               5                  10                  15

Ser Ser Ala Gly Ser Ile Leu Gly Arg Ser Glu Thr Lys Glu Cys Ile
            20                  25                  30

Tyr Tyr Asn Ala Asn Trp Glu Lys Asp Lys Thr Asn Ser Asn Gly Thr
        35                  40                  45

Glu Ile Cys Tyr Gly Asp Asn Asp Lys Arg Lys His Cys Phe Ala Thr
    50                  55                  60

Trp Lys Asn Ile Ser Gly Ser Ile Glu Ile Val Lys Gln Gly Cys Trp
65                  70                  75                  80

Leu Asp Asp Ile Asn Cys Tyr Asn Lys Ser Lys Cys Thr Glu Lys Lys
                85                  90                  95

Asp Ser Pro Asp Val Phe Phe Cys Cys Cys Glu Gly Asn Tyr Cys Asn
            100                 105                 110

Glu Lys Phe Tyr His Ser Pro Glu Met Glu Val Thr Gln Pro Thr Ser
        115                 120                 125

Asn Pro Val Thr Thr Lys Pro Pro Leu Phe Asn Thr Leu Leu Tyr Ser
    130                 135                 140

Leu Val Pro Ile Met Val Val Ala Val Ile Val Leu Phe Ser Phe Trp
145                 150                 155                 160

Met Tyr Arg His His Lys Leu Ala Tyr Pro Pro Val Leu Val Pro Thr
                165                 170                 175

Gln Asp Pro Gly Pro Pro Pro Ser Pro Leu Leu Gly Leu Lys Pro
            180                 185                 190

Leu Gln Leu Leu Glu Val Lys Ala Arg Gly Arg Phe Gly Cys Val Trp
        195                 200                 205

Lys Ala Gln Leu Leu Asn Glu Thr Val Ala Val Lys Ile Phe Pro Val
    210                 215                 220

Gln Asp Lys Leu Ser Trp Gln Asn Glu Tyr Glu Ile Tyr Ser Leu Pro
```

-continued

```
225                 230                 235                 240
Gly Met Lys His Glu Asn Ile Leu Tyr Phe Ile Gly Ala Glu Lys Arg
                245                 250                 255
Gly Thr Asn Leu Asp Thr Asp Leu Trp Leu Ile Thr Ala Phe His Glu
                260                 265                 270
Lys Gly Ser Leu Thr Asp Tyr Leu Lys Ala Asn Val Val Ser Trp Asn
                275                 280                 285
Glu Leu Cys Leu Ile Ala Glu Thr Met Ala Arg Gly Leu Ser His Leu
                290                 295                 300
His Glu Asp Ile Pro Gly Leu Lys Asp Gly His Lys Pro Ala Val Ala
305                 310                 315                 320
His Arg Asp Ile Lys Ser Lys Asn Val Leu Leu Lys Asn Asn Leu Thr
                325                 330                 335
Ala Cys Ile Ala Asp Phe Gly Leu Ala Leu Lys Phe Glu Ala Gly Lys
                340                 345                 350
Ser Ala Gly Asp Thr His Gly Gln Val Gly Thr Arg Arg Tyr Met Ala
                355                 360                 365
Pro Glu Val Leu Glu Gly Ala Ile Asn Phe Gln Arg Asp Ala Phe Leu
    370                 375                 380
Arg Ile Asp Met Tyr Ala Phe Gly Leu Val Leu Trp Glu Leu Ala Ser
385                 390                 395                 400
Arg Cys Thr Ala Ser Asp Gly Pro Val Asp Glu Tyr Met Leu Pro Phe
                405                 410                 415
Glu Glu Glu Val Gly Gln His Pro Ser Leu Glu Asp Met Gln Glu Val
                420                 425                 430
Val Val His Lys Lys Lys Arg Pro Ile Leu Arg Glu Cys Trp Gln Lys
                435                 440                 445
His Ala Gly Met Ala Met Leu Cys Glu Thr Ile Glu Glu Cys Trp Asp
    450                 455                 460
His Asp Ala Glu Ala Arg Leu Ser Ala Gly Cys Val Glu Glu Arg Ile
465                 470                 475                 480
Ile Gln Met Gln Lys Leu Thr Asn Ile Ile Thr Thr Glu Asp Ile Val
                485                 490                 495
Thr Val Val Thr Met Val Thr Asn Val Asp Phe Pro Pro Lys Glu Ser
                500                 505                 510
Ser Leu
```

DNA ENCODING A NEURONAL CELL-SPECIFIC RECEPTOR PROTEIN

TECHNICAL FIELD

The present invention relates to a receptor protein having a particular amino acid sequence, particularly a new neuronal cell-specific receptor, more particularly a new activin receptor protein, DNA containing a DNA region encoding said protein, a production method for said protein, a detection method for the gene encoding said protein, and use for said protein and DNA.

BACKGROUND ART

To date, numerous bioactive substances exhibiting diverse actions on various organs and cells have been isolated and identified, and their functions elucidated. The diverse bioactivity of these substances in various organs and cells is normally expressed via receptors to which they are bound; however, it remains unknown as to whether all organs and cells share the same receptors or if the organ and cell specificity of receptors is variable.

Steroid hormones produced by reproductive glands were assumed to be responsible for the regulation of gonadotropic hormone secretion from the pituitary gland. Then activin was first isolated as a regulator that promotes the secretion of follicle-stimulating hormone (FSH) from the anterior lobe of the pituitary gland. After the discovery of activin and inhibin, which antagonizes activin, activin and inhibin have drawn attention as facilitating a new mechanism of hormone secretion regulation for the hypothalamus-pituitary-reproductive organ system. Analysis of the bioactivity of activin has revealed various biological actions, including induction or inhibition of cell differentiation in the blood cell system and reproductive organs, and neuronal cell survival maintenance action, in addition to regulation of FSH secretion. However, much remains unknown as to activin's detailed mechanism of action.

The activin receptor gene has been cloned in humans, mice, rats and other animals and structural analysis has revealed two types: types I and II. It has also been shown that types I and II each have two subtypes, A and B, and that type IIB can be divided into four subtypes by alternative splicing. Receptor proteins assumed to mediate the diverse bioactivity of activin have varying affinity for different forms of activin; their expression is known to occur over a wide range without organ or cell specificity. Activin is known to induce or inhibit cell differentiation, but the expression of activin or its receptors has not been known to significally vary during all differentiation. The mechanism of diverse actions of activin remains to be elucidated in detail.

SUMMARY OF THE INVENTION

The object of the present invention is to develop a method for elucidating the function of receptors, especially neuronal cell-specific receptors, more specifically to provide an isolation and detection method for a new nerve system-specific activin receptor gene, DNA containing said new activin receptor gene, a production method for a protein encoded by said new activin receptor gene, and use for said DNA and said protein, as a tool for elucidating the detailed mechanism of neuronal cell differentiation inhibition and nerve nutrition factor-like action of activin receptors.

With the aim of solving the above problems, the present inventors made extensive investigation, and succeeded in amplifying a cDNA fragment encoding activin receptor type IIA protein from poly(A)+ RNA from P19, a mouse embryonal carcinoma cell line whose neuronal differentiation was induced with retinoic acid by reverse transcriptase polymerase chain reaction; (hereinafter referred to as the RT-PCR method) using synthetic DNA primers for efficient isolation of cDNA encoding activin receptor type IIA protein. As a result of analysis of the cDNA fragment, the present inventors isolated DNA encoding a new receptor protein. Further analysis of the base sequence of the DNA demonstrated that said DNA encodes a new receptor protein containing eight amino acids shown by SEQ ID NO:7. The present inventors made further investigation, and found that said receptor gene is specifically expressed in neuronal cells and organs.

The present inventors also found that the expression of the known activin receptor type IIA gene and that of said new receptor gene can easily be differentiated and separately detected by the RT-PCR method using said synthetic DNA primers.

More specifically, the present inventors obtained cDNA fragments from poly(A)+ RNA from P19, a mouse embryonal carcinoma cell line whose neuronal differentiation was induced with retinoic acid, by the RT-PCR method using as primers the two synthetic DNAs shown by SEQ ID NO:1 and SEQ ID NO:2 selected from the known mouse activin receptor type IIA gene shown in FIG. 1A and FIG. 1B and FIG. 2A and FIG. 2B (M65287, GenBank data registration number), resulting in the amplification of a longer cDNA fragment, together with a fragment having the same length as that of the fragment deduced from the known base sequence (neucleotide sequence). This longer cDNA fragment was subjected to base sequence analysis. The present inventors found that these two cDNAs respectively encode the known activin receptor type IIA gene (M65287) and a new receptor wherein the 24 bp sequence shown by SEQ ID NO:3 is inserted to the splicing site of the known activin receptor type IIA gene (M65287).

Next, the present inventors prepared cDNA from poly (A)+ RNA from P19, a mouse embryonal carcinoma cell line whose neuronal differentiation was induced with retinoic acid, and inserted it into λZAPII phage to yield a cDNA library. The present inventors further screened this library using as a probe the cDNA having a 24 bp sequence which was inserted to the splicing site of the known activin receptor type IIA gene (M65287), obtained by the RT-PCR method, and obtained a DNA fragment encoding the entire new receptor protein of the present invention. This DNA fragment was subjected to base sequence analysis, resulting in the finding that its base sequence was identical to that of the activin receptor type IIA gene (M65287), except for the 24 bp insertion discovered by the present inventors, as shown by SEQ ID NO:4, and that the amino acid sequence deduced therefrom is shown by SEQ ID NO:5 (see FIGS. 3 through 6).

The present inventors further extracted poly(A)+ RNA from various mouse organs, and examined the expression of the present new receptor by the RT-PCR method using as primers the synthetic DNAs shown by SEQ ID NO:1 and SEQ ID NO:2, resulting in the finding that its expression is specific to the neuronal system (e.g. brain) and the whole embryo, as shown in FIG. 7.

In addition, the present inventors obtained cDNA fragments by the RT-PCR method using as primers the synthetic DNAs shown by SEQ ID NO:1 and SEQ ID No:2 from poly(A)+ RNA from a human neuroblastoma cell line, and obtained cDNA fragments by the RT-PCR method using as primers the synthetic DNAs shown by SEQ ID NO:9 and SEQ ID NO:10 from poly(A)+ RNA from frog embryo, and found that longer cDNA fragments were amplified, together with those of the same length as that of the fragment deduced from the known base sequence, as described above. These cDNA fragments were subjected to base sequence analysis, resulting in the finding that the same 24 bp sequence was inserted both in humans and frogs, and that the base sequence in humans is identical to that in mice, while the base sequence in frogs is the base sequence shown by SEQ ID NO:6. The present inventors also found that these base sequences shown by SEQ ID NO:3 and SEQ ID NO:6, when translated to amino acid sequences, correspond to the amino acid sequence shown by SEQ ID NO:7, i.e., the amino acid sequence is preserved to very high degree without species specificity.

Accordingly, the present invention provides:

(1) A receptor protein containing an amino acid sequence substantially shown by the formula;

His Ala Phe His Ile Met Ile Glu            (SEQ ID NO:7)

or a salt thereof, (2) the protein described in the above item (1) wherein said receptor protein is a neuronal cell-specific receptor protein, (3) the protein described in the above item (2) wherein said receptor protein is an activin receptor protein, (4) a receptor protein containing or comprising an amino acid sequence shown by

```
X-  Gly Ala Ala Ala Lys Leu Ala Phe Ala Val Phe Leu Ile Ser Cys   (SEQ ID NO:5)

Ser Ser Gly Ala Ile Leu Gly Arg Ser Glu Thr Gln Glu Cys Leu Phe

Phe Asn Ala Asn Trp Glu Arg Asp Arg Thr Asn Gln Thr Gly Val Glu

Pro Cys Tyr Gly Asp Lys Asp Lys Arg Arg His Cys Phe Ala Thr Trp

Lys Asn Ile Ser Gly Ser Ile Glu Ile Val Lys Gln Gly Cys Trp Leu

Asp Asp Ile Asn Cys Tyr Asp Arg Thr Asp Cys Ile Glu Lys Lys Asp

Ser Pro Glu Val Tyr Phe Cys Cys Cys Glu Gly Asn Met Cys Asn Glu

Lys Phe Ser Tyr Phe Pro Glu Met Glu Val Thr Gln Pro Thr Ser Asn

Pro Val Thr Pro Lys Pro Pro Tyr Tyr Asn Ile Leu Leu Tyr Ser Leu

Val Pro Leu Met Leu Ile Ala Gly Ile Val Ile Cys Ala Phe Trp Val

Tyr Arg His His Lys Met Ala Tyr Pro Pro Val Leu Val Pro Thr Gln

His Ala Phe His Ile Met Ile Glu Asp Pro Gly Pro Pro Pro Pro Ser

Pro Leu Leu Gly Leu Lys Pro Leu Gln Leu Leu Glu Val Lys Ala Arg

Gly Arg Phe Gly Cys Val Trp Lys Ala Gln Leu Leu Asn Glu Tyr Val

Ala Val Lys Ile Phe Pro Ile Gln Asp Lys Gln Ser Trp Gln Asn Glu

Tyr Glu Val Tyr Ser Leu Pro Gly Met Lys His Glu Asn Ile Leu Gln

Phe Ile Gly Ala Glu Lys Arg Gly Thr Ser Val Asp Val Asp Leu Trp

Leu Ile Thr Ala Phe His Glu Lys Gly Ser Leu Ser Asp Phe Leu Lys

Ala Asn Val Val Ser Trp Asn Glu Leu Cys His Ile Ala Glu Thr Met

Ala Arg Gly Leu Ala Tyr Leu His Glu Asp Ile Pro Gly Leu Lys Asp

Gly His Lys Pro Ala Ile Ser His Arg Asp Ile Lys Ser Lys Asn Val

Leu Leu Lys Asn Asn Leu Thr Ala Cys Ile Ala Asp Phe Gly Leu Ala

Leu Lys Phe Glu Ala Gly Lys Ser Ala Gly Asp Thr His Gly Gln Val

Gly Thr Arg Arg Tyr Met Ala Pro Glu Val Leu Glu Gly Ala·Ile Asn

Phe Gln Arg Asp Ala Phe Leu Arg Ile Asp Met Tyr Ala Met Gly Leu

Val Leu Trp Glu Leu Ala Ser Arg Cys Thr Ala Ala Asp Gly Pro Val

Asp Glu Tyr Met Leu Pro Phe Glu Glu Ile Gly Gln His Pro Ser

Leu Glu Asp Met Gln Glu Val Val Val His Lys Lys Lys Arg Pro Val

Leu Arg Asp Tyr Trp Gln Lys His Ala Gly Met Ala Met Leu Cys Glu
```

```
Thr Ile Glu Glu Cys Trp Asp His Asp Ala Glu Ala Arg Leu Ser Ala

Gly Cys Val Gly Glu Arg Ile Thr Gln Met Gln Arg Leu Thr Asn Ile

Ile Thr Thr Glu Asp Ile Val Thr Val Val Thr Met Val Thr Asn Val

Asp Phe Pro Pro Lys Glu Ser Ser Leu,
``` wherein X represents Met that may be protected or hydrogen, or any portion thereof which also contains the amino acid sequence substantially shown by the formula: His Ala Phe His Ile Met Ile Glu, (SEQ ID NO:7) or a salt thereof, (5) the protein described in the above item (3) having an amino acid sequence shown by

```
X-  Gly Ala Ala Ala Lys Leu Ala Phe Ala Val Phe Leu Ile Ser Cys   (SEQ ID NO:5)

Ser Ser Gly Ala Ile Leu Gly Arg Ser Glu Thr Gln Glu Cys Leu Phe

Phe Asn Ala Asn Trp Glu Arg Asp Arg Thr Asn Gln Thr Gly Val Glu

Pro Cys Tyr Gly Asp Lys Asp Lys Arg Arg His Cys Phe Ala Thr Trp

Lys Asn Ile Ser Gly Ser Ile Glu Ile Val Lys Gln Gly Cys Trp Leu

Asp Asp Ile Asn Cys Tyr Asp Arg Thr Asp Cys Ile Glu Lys Lys Asp

Ser Pro Glu Val Tyr Phe Cys Cys Cys Glu Gly Asn Met Cys Asn Glu

Lys Phe Ser Tyr Phe Pro Glu Met Glu Val Thr Gln Pro Thr Ser Asn

Pro Val Thr Pro Lys Pro Pro Tyr Tyr Asn Ile Leu Leu Tyr Ser Leu

Val Pro Leu Met Leu Ile Ala Gly Ile Val Ile Cys Ala Phe Trp Val

Tyr Arg His His Lys Met Ala Tyr Pro Pro Val Leu Val Pro Thr Gln

His Ala Phe His Ile Met Ile Glu Asp Pro Gly Pro Pro Pro Pro Ser

Pro Leu Leu Gly Leu Lys Pro Leu Gln Leu Leu Glu Val Lys Ala Arg

Gly Arg Phe Gly Cys Val Trp Lys Ala Gln Leu Leu Asn Glu Tyr Val

Ala Val Lys Ile Phe Pro Ile Gln Asp Lys Gln Ser Trp Gln Asn Glu

Tyr Glu Val Tyr Ser Leu Pro Gly Met Lys His Glu Asn Ile Leu Gln

Phe Ile Gly Ala Glu Lys Arg Gly Thr Ser Val Asp Val Asp Leu Trp

Leu Ile Thr Ala Phe His Glu Lys Gly Ser Leu Ser Asp Phe Leu Lys

Ala Asn Val Val Ser Trp Asn Glu Leu Cys His Ile Ala Glu Thr Met

Ala Arg Gly Leu Ala Tyr Leu His Glu Asp Ile Pro Gly Leu Lys Asp

Gly His Lys Pro Ala Ile Ser His Arg Asp Ile Lys Ser Lys Asn Val

Leu Leu Lys Asn Asn Leu Thr Ala Cys Ile Ala Asp Phe Gly Leu Ala

Leu Lys Phe Glu Ala Gly Lys Ser Ala Gly Asp Thr His Gly Gln Val

Gly Thr Arg Arg Tyr Met Ala Pro Glu Val Leu Glu Gly Ala Ile Asn

Phe Gln Arg Asp Ala Phe Leu Arg Ile Asp Met Tyr Ala Met Gly Leu

Val Leu Trp Glu Leu Ala Ser Arg Cys Thr Ala Ala Asp Gly Pro Val

Asp Glu Tyr Met Leu Pro Phe Glu Glu Ile Gly Gln His Pro Ser

Leu Glu Asp Met Gln Glu Val Val Val His Lys Lys Lys Arg Pro Val

Leu Arg Asp Tyr Trp Gln Lys His Ala Gly Met Ala Met Leu Cys Glu

Thr Ile Glu Glu Cys Trp Asp His Asp Ala Glu Ala Arg Leu Ser Ala
```

-continued

```
Gly Cys Val Gly Glu Arg Ile Thr Gln Met Gln Arg Leu Thr Asn Ile

Ile Thr Thr Glu Asp Ile Val Thr Val Val Thr Met Val Thr Asn Val

Asp Phe Pro Pro Lys Glu Ser Ser Leu,
``` wherein X represents Met that may be protected or hydrogen; or a salt thereof, (6) a protein containing an amino acid sequence substantially comprised of amino acid residues His Ala Phe His Ile Met Ile Glu (SEQ ID NO:7), wherein said protein is capable of binding with activin or activin like substances or a portion thereof, (7) an isolated and purified DNA sequence encoding a protein containing an amino acid sequence sufficiently duplicative of the sequence His Ala Phe His Ile Met Ile Glu to allow possession of the biological property of binding with activin or activin containing substances, (8) a DNA containing a nucleotide sequence encoding the protein described in the above item (1), (9) the DNA described in the above item (8), containing a nucleotide sequence shown by

```
X'  GGA GCT GCT GCA AAG TTG GCG TTC GCC GTC TTT CTT ATC TCT TGC  (SEQ ID NO:11)

TCT TCA GGT GCT ATA CTT GGC AGA TCA GAA ACT CAG GAG TGT CTT TTC

TTT AAT GCT AAT TGG GAA AGA GAC AGA ACC AAC CAG ACT GGT GTT GAA

CCT TGC TAT GGT GAT AAA GAT AAA CGG CGA CAT TGT TTT GCT ACC TGG

AAG AAT ATT TCT GGT TCC ATT GAA ATA GTG AAG CAA GGT TGT TGG CTG

GAT GAT ATC AAC TGC TAT GAC AGG ACT GAT TGT ATA GAA AAA AAA GAC

AGC CCT GAA GTG TAC TTT TGT TGC TGT GAG GGC AAT ATG TGT AAT GAA

AAG TTC TCT TAT TTT CCG GAG ATG GAA GTC ACA CAG CCC ACT TCA AAT

CCT GTT ACA CCG AAG CCA CCC TAT TAC AAC ATT CTG CTG TAT TCC TTG

GTA CCA CTA ATG TTA ATT GCA GGA ATT GTC ATT TGT GCA TTT TGG GTG

TAC AGA CAT CAC AAG ATG GCC TAC CCT CCT GTA CTT GTT CCT ACT CAA

CAC GCC TTT CAT ATA ATG ATA GAG GAC CCA GGA CCA CCC CCA CCT TCC

CCA TTA CTA GGG TTG AAG CCA TTG CAG CTG TTA GAA GTG AAA GCA AGG

GGA AGA TTT GGT TGT GTC TGG AAA GCC CAG TTG CTC AAT GAA TAT GTG

GCT GTC AAA ATA TTT CCA ATA CAG GAC AAA CAG TCC TGG CAG AAT GAA

TAT GAA GTC TAT AGT CTA CCT GGA ATG AAG CAT GAG AAC ATA CTA CAG

TTC ATT GGT GCA GAG AAA AGA GGC ACC AGT GTG GAT GTG GAC CTG TGG

CTA ATC ACA GCA TTT CAT GAA AAG GGC TCA CTG TCA GAC TTT CTT AAG

GCT AAT GTG GTC TCT TGG AAT GAA CTT TGT CAT ATT GCA GAA ACC ATG

GCT AGA GGA TTG GCA TAT TTA CAT GAG GAT ATA CCT GGC TTA AAA GAT

GGC CAC AAG CCT GCA ATC TCT CAC AGG GAC ATC AAA AGT AAA AAT GTG

CTG TTG AAA AAC AAT CTG ACA GCT TGC ATT GCT GAC TTT GGG TTG GCC

TTA AAG TTC GAG GCT GGC AAG TCT GCA GGT GAC ACC CAT GGG CAG GTT

GGT ACC CGG AGG TAT ATG GCT CCA GAG GTG TTG GAG GGT GCT ATA AAC

TTC CAA AGG GAC GCA TTT CTG AGG ATA GAT ATG TAC GCC ATG GGA TTA

GTC CTA TGG GAA TTG GCT TCT CGT TGC ACT GCT GCA GAT GGA CCC GTA

GAT GAG TAC ATG TTA CCA TTT GAG GAA GAA ATT GGC CAG CAT CCA TCT

CTT GAA GAT ATG CAG GAA GTT GTT GTG CAT AAA AAA AAG AGG CCT GTT

TTA AGA GAT TAT TGG CAG AAA CAT GCA GGA ATG GCA ATG CTC TGT GAA
```

-continued

```
ACG ATA GAA GAA TGT TGG GAT CAT GAT GCA GAA GCC AGG TTA TCA GCT

GGA TGT GTA GGT GAA AGA ATT ACT CAG ATC CAA AGA CTA ACA AAT ATC

ATT ACT ACA GAG GAC ATT GTA ACA GTG GTC ACA ATG GTG ACA AAT GTT

GAC TTT CCT CCC AAA GAA TCT AGT CTA,
``` wherein X' represents ATG or hydrogen,

(10) a vector containing the DNA described in the above item (8),

(11) a transformant harboring the vector described in the above item (10),

(12) a method of producing the protein described in the above item (1) by culturing the transformant described in the above item (11) to produce and accumulate the protein or a salt thereof in the culture, and collecting said protein,

(13) a method of producing the protein described in the above item (1) by culturing the transformant described in the above item (11) to produce and accumulate the protein or a salt thereof in the culture supernatant or on the transformant's cell membrane, and collecting said protein,

(14) a method of detecting the DNA described in the above item (8) characterized by conducting the polymerase chain reaction method using synthetic DNA containing the base sequence of the formula:

TACCCTCCTGTACTTGTTCCTACTCAA    (SEQ ID NO:1)

and the formula:

TAGCCACAGGTCCACATCCACACTGGT,    (SEQ ID NO:2)

(15) an antibody against the protein described in the above item (1),

(16) a method of quantifying the protein described in the above item (1) by competitively reacting a subject solution containing the protein described in the above item (1) and the labeled protein in the above item (1) to the antibody in the above item (15),

(17) a method of determining a ligand against the protein described in the above item (1), wherein the protein described in the above item (1) is brought into contact with a test compound,

(18) a method of screening for a compound that inhibits or promotes the binding of the protein described in the above item (1) with a ligand wherein comparison is made between the binding affinities achieved in case (i) in which the ligand is brought into contact with the protein described in the above item (1), and case (ii) in which both the ligand and the compound are brought into contact with the protein described in the above item (1),

(19) a screening kit containing the protein described in the above item (1) and a ligand against the protein described in the above item (1), which screens for a compound that inhibits or promotes (i) the binding of a ligand against the protein described in the above item (1) or (ii) the binding of a ligand against a known activin receptor protein or a salt thereof,

(20) an activin receptor agonist or activin receptor antagonist obtained by using the screening method described in the above item (18) and/or the screening kit described in the above item (19),

(21) a diagonistic method for nerve degeneration disease wherein the DNA detection method described in the above item (14) is used.

BRIEF DESCRIPTION OF THE DRAWINGS

FIG. 2A and FIG. 2B show the last half of the entire base sequence of cDNA encoding the mouse activin receptor type IIA (ATR) protein and the last half of the amino acid sequence deduced therefrom. (Continued from FIG. 1A and FIG. 1B). The entire base sequence of the cDNA encoding the mouse activin type II receptor is referenced as SEQ ID NO: 12. The mouse activin type II receptor protein is referenced as SEQ ID NO: 13.

FIG. 3 shows the first half of the entire base sequence of new receptor cDNA obtained from mouse embryonal carcinoma cell line P19 undergoing neuronal differentiation with retinoic acid by the RT-PCR method. (To be continued to FIG. 4)

FIG. 4 shows the last half of the entire base sequence of new receptor cDNA obtained from mouse embryonal carcinoma cell line P19 undergoing neuronal differentiation with retinoic acid by the RT-PCR method. (Continued from FIG. 3). The entire base sequence of the cDNA encoding the new receptor obtained from mouse embryonal carcinoma cell line P19 is referenced as SEQ ID NO: 4.

FIG. 5 shows the first half of the amino acid sequence deduced from the base sequence shown in FIGS. 3 and 4. (To be continued to FIG. 6)

FIG. 6 shows the last half of the amino acid sequence deduced from the base sequence shown in FIGS. 3 and 4. (Continued from FIG. 5) The entire amino acid sequence deduced from the base sequence shown in FIGS. 3 and 4 is referenced as (SEQ ID NO: 5).

FIG. 8A and FIG. 8B show the first half of the entire base sequence of cDNA encoding frog activin receptor type II protein. (To be continued to FIG. 9A and FIG. 2B)

FIG. 9A and FIG. 9B show the last half of the entire base sequence of cDNA encoding frog activin receptor type II protein. (Continued from FIG. 8A and FIG. 8B)

DETAILED DESCRIPTION OF THE INVENTION

Figure 1:
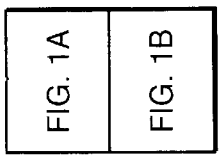
FIG. 1A and FIG. 1B show the first half of the entire base sequence of cDNA encoding the mouse activin receptor type IIA (ATR) protein and the first half of the amino acid sequence deduced therefrom. Underlined portion (single line) indicates the position of the synthetic primer used for RT-PCR. (To be continued to FIG. 2A and FIG. 2B)

The receptor protein, especially, the neuronal cell-specific receptor protein of the present invention may be any protein, as long as it contains the amino acid sequence substantially shown by SEQ ID NO:7, but preference is given to activin receptor protein. The amino acid sequence substantially shown by SEQ ID NO:7 possesses substantially the same activity as that of a protein containing the amino acid sequence shown by SEQ ID NO:7, and is exemplified by amino acid sequences resulting from deletion of 1 or more (preferably 1 or 2, more preferably 1) amino acid(s) from the amino acid sequence shown by SEQ ID NO:7, amino acid sequences resulting from addition or insertion of 1 or more (preferably 1 or 2, more preferably 1) amino acid(s) to the amino acid sequence shown by SEQ ID NO:7, and amino acid sequences resulting from replacement with other amino acids of 1 or more (preferably 1 or 2, more preferably 1) amino acid(s) from the amino acid sequence shown by SEQ ID NO:7. Any receptor protein serves for the present invention, as long as it is derived from any tissue (e.g., stomach, pituitary, spleen, brain, kidney, liver, reproductive gland, thyroid gland, gallbladder, bone marrow, adrenal, skin, muscle, lung, digestive tract, blood vessel, heart) or cell of warm-blooded animals (e.g., guinea pigs, rats, mice, rabbits, pigs, sheep, bovines, monkeys, humans) and as long it contains the amino acid sequence substantially shown by SEQ ID NO:7, but preference is given to one having substantially the same amino acid sequence as the amino acid sequence shown by SEQ ID NO:5. In other words, the receptor protein of the present invention may have any length, as long as it contains the amino acid sequence substantially shown by SEQ ID NO:7. Specifically, the receptor protein of the present invention may have a length of the peptide shown by SEQ ID NO:7, which is of the 8-amino acid sequence length, to a length of the amino acid sequence shown by SEQ ID NO:5, which is 521 amino acids in length, or longer. Preferable proteins include those that contain both the amino acid sequence substantially shown by SEQ ID NO:7 and an amino acid sequence possessing about 80–99.9% homology to the amino acid sequence shown by SEQ ID NO:5, and that possess substantially the same activity as that of a protein containing the amino acid sequence shown by SEQ ID NO:5, with greater preference given to proteins that contain the amino acid sequence substantially shown by SEQ ID NO:7, that has an amino acid sequence, without interruption, between the N- and C-ends of the amino acid sequence shown by SEQ ID NO:5 wherein one of the first amino acid (Met) through the 105th amino acid (Cys) of the 521-amino acid sequence shown by SEQ ID NO:5 constitutes the N-end and one of the 417th amino acid (Asp) through the 521st amino acid (Leu) constitutes the C-end, and that has an amino acid sequence length of not shorter than 417 amino acids. The first amino acid (Met) of the amino acid sequence shown by SEQ ID NO:5 may be protected or converted to hydrogen. Substantially the same activity is exemplified by ligand-binding activity and signal information transmission. Quantitative factors, such as ligand binding activity strength and receptor protein molecular weight may therefore differ.

More specifically, the receptor protein of the present invention (neuronal cell-specific receptor protein, more preferably activin receptor protein) is exemplified by the activin receptor protein from P19, a mouse embryonal carcinoma cell line, which contains the amino acid sequence shown by SEQ ID NO:5. The receptor protein of the present invention is also exemplified by amino acid sequences resulting from deletion of 1 or more (preferably 2 to 30, more preferably 2 to 10) amino acids from the amino acid sequence shown by SEQ ID NO:5 but other than SEQ ID NO:7, amino acid sequences resulting from addition or insertion of 1 or more (preferably 2 to 30, more preferably 2 to 10) amino acids to amino acid sequences other than SEQ ID NO:7 in SEQ ID NO:5, and amino acid sequences resulting from replacement with other amino acids of 1 or more (preferably 2 to 30, more preferably 2 to 10) amino acids from SEQ ID NO:5 but other than SEQ ID NO:7. The receptor protein of the present invention is still further exemplified by proteins wherein the N-terminal Met has been converted to H, those wherein the N-terminal Met is protected by a protecting group (e.g., $C_{1-6}$ acyl group such as formyl group or acetyl group, preferably $C_{1-6}$ alkanoyl group), those wherein the N-terminal side of Glu has been cleaved in the body, resulting in the formation of pyroglutamated Glu, those wherein the intramolecular amino acid side chain is protected by an appropriate protective group (e.g., $C_{1-6}$ acyl group such as formyl group or acetyl group, preferably $C_{1-6}$ alkanoyl group), and complex proteins such as glycoproteins resulting from binding of a sugar chain.

The salt of the receptor protein of the present invention (preferably neuronal cell-specific receptor protein, more preferably activin receptor protein) is preferably a physiologically acceptable acid adduct salt. Such salts include salts with inorganic acids (e.g., hydrochloric acid, phosphoric acid, hydrobromic acid, sulfuric acid) and salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid).

The receptor protein of the present invention or a salt thereof can be produced from warm-blooded animal tissue or cells by a commonly known method of protein purification, or by culturing the transformant described below, which contains DNA encoding an activin receptor protein. It can also be produced in accordance with the method of peptide synthesis described below.

The peptide of the present invention containing the amino acid sequence shown by SEQ ID NO:7 or a salt thereof can be produced by a commonly known method of peptide synthesis, or by cleaving the activin receptor protein of the present invention using an appropriate peptidase. As the peptide synthesis both solid-phase synthesis and liquid-phase synthesis are applicable. In other words, the desired peptide can be produced by condensing together a partial peptide or amino acid capable of constituting the protein of the present invention and the remaining portion, and, when the product has a protecting group, eliminating the protecting group. Useful methods of condensation or protecting group elimination are described in the following references ① through ⑤.

① M. Bodanszky and M. A. Ondetti, Peptide Synthesis, Interscience Publishers, New York (1966)
② Schroeder and Luebke, The Peptide, Academic Press, New York (1965)
③ Nobuo Izumiya et al., Peptide Gosei no Kiso to Jikken, Maruzen (1975)
④ Haruaki Yajima and Shunpei Sakakibara, Seikagaku Jikken Koza 1, Tanpakushitsu no Kagaku, 205 (1977).
⑤ Haruaki Yajima ed., Zoku Iyakuhin no Kaihatsu, Vol. 14, Peptide Gosei, Hirokawa Shoten The reaction may be followed by a combination of ordinary purification methods such as solvent extraction, distillation, column chromatography, liquid chromatography and recrystallization to purify and isolate the protein of the present invention. When the protein is obtained in free form, it can be converted to an appropriate salt by a known method; when the protein is obtained in salt form, it can be converted to free form by a known method.

Any DNA encoding the receptor protein of the present invention may be used, as long as it contains a base sequence encoding an activin receptor protein and containing both the amino acid sequence of the present invention of SEQ ID NO:7 and substantially the same amino acid sequence as the amino acid sequence of the amino acid sequence of SEQ ID NO:5. It may be one wherein the 5'-terminal ATG has been converted to H. It may also be genomic DNA of warm-blood animals (e.g., humans), genomic DNA library of warm-blooded animals (e.g., humans), tissue/cell-derived cDNA of warm-blooded animals (e.g., humans), tissue/cell-derived cDNA library of warm-blooded animals (e.g., humans), or synthetic or semi-synthetic DNA. The vector used for the library may be bacteriophage, plasmid, cosmid, phagemid, or the like. Also, direct amplification by the RT-PCR method is also possible using a preparation of mRNA fraction prepared from tissue or cells. Alternatively, the desired DNA can be produced by chemically synthesizing individual partial base sequences and condensing them together.

More specifically, DNA having the base sequence shown by SEQ ID NO:4, or the like, is used as the DNA encoding the activin receptor protein from P19, a mouse embryonal carcinoma cell line, which has the amino acid sequence of SEQ ID NO:5.

Cloning of DNA encoding the entire portion of the receptor protein of the present invention can be achieved by amplifying the subject DNA by the PCR method using a synthetic DNA primer having a partial base sequence of the receptor protein, or selecting the desired DNA by hybridization of DNA incorporated in an appropriate vector with a DNA fragment having a partial or entire region of the receptor protein or with a DNA fragment labeled with synthetic DNA. This hybridization is carried out by, for example, the method described in Molecular Cloning, 2nd edition, J. Sambrook et al., Cold Spring Harbor Laboratory Press, 1989. When a commercially available library is used, hybridization is carried out as directed in the instruction manual attached to the kit. The cloned DNA encoding the receptor protein can be used as such, or after restriction enzyme digestion or linker addition as appropriate, depending on the purpose of use. Said DNA may have the translation initiation codon ATG on the 5'-terminal side thereof and the translation termination codon TAA, TGA or TAG on the 3'-terminal side thereof. These translation initiation codon and translation termination codons may also be added using an appropriate synthetic DNA adaptor.

An expression vector for the activin receptor protein can, for example, be produced by (a) excising the desired DNA fragment from DNA encoding the activin receptor protein of the present invention, and (b) ligating said DNA fragment downstream a promoter in an appropriate expression vector. Useful vectors include plasmids derived from *Escherichia coli* (e.g., pBR322, pBR325, pUC12, pUC13), plasmids derived from *Bacillus subtilis* (e.g., pUB110, pTP5, pC194), yeast-derived plasmids (e.g., pSH19, pSH15), bacteriophages such as λ phage, and animal viruses such as retrovirus, vaccinia virus and baculovirus.

Any promoter can be used for the present invention, as long as it is appropriate for the host used to express the desired gene.

Preferred promoters include the trp promoter, lac promoter, recA promoter, λPL promoter and lpp promoter, when the transformation host is a bacterium of the genus Escherichia; the SPO1 promoter, SPO2 promoter-and penP promoter when the host is a bacterium of the genus Bacillus; and the pHO5 promoter, PGK promoter, GAP promoter and ADH promoter when the host is a yeast.

When the host is an animal cell, the SV40-derived promoter, retrovirus promoter, metallothionein promoter, heat shock promoter, cytomegalovirus promoter, SRα promoter etc. can be advantageously used. Expression is also effected by the use of an enhancer.

Also, a signal sequence corresponding to the host may be added to the N-terminal side of the receptor protein as necessary. Useful signal sequences include alkaline phosphatase signal sequence and OmpA signal sequence when the host is a bacterium of the genus Escherichia; α-amylase signal sequence and subtilin signal sequence when the host is a bacterium of the genus Bacillus; the mating factor α signal sequence and invertase signal sequence when the host is a yeast; and the insulin signal sequence, α-interferon signal sequence and antibody molecule signal sequence when the host is an animal cell.

The thus-constructed vector containing DNA encoding the receptor protein is used to produce a transformant. Examples of the host include bacteria of the genus Escherichia, bacteria of the genus Bacillus, yeasts, insects and animal cells.

Examples of the bacteria of the genus Escherichia include *Escherichia coli* K12·DH1 [Proceedings of the National Academy of Sciences of the USA, Vol. 60, 160 (1968)], JM103 [Nucleic Acids Research, Vol. 9, 309 (1981)], JA221 [Journal of Molecular Biology, Vol. 120, 517 (1978)], HB101 [Journal of Molecular Biology, Vol. 41, 459 (1969)] and C600 [Genetics, Vol. 39, 440 (1954)].

Examples of the bacteria of the genus Bacillus include *Bacillus subtilis* MI114 [Gene, Vol. 24, 255 (1983)] and 207–21 [Journal of Biochemistry, Vol. 95, 87 (1984)].

Examples of the yeasts include *Saccharomyces cerevisiae* AH22, AH22R⁻, NA87-11A, DKD-5D and 20B-12.

Examples of the insects include silkworm larvae [Maeda et al., Nature, Vol. 315, 592 (1985)].

Examples of the animal cells include simian COS-7 cells, Vero cells, Chinese hamster CHO cells, DHFR gene deficient Chinese hamster CHO cells (dhfr⁻ CHO cells), mouse L cells, mouse myeloma cells and human FL cells. The bacteria of the genus Escherichia can be transformed in accordance with the method described in the Proceedings of the National Academy of Sciences of the USA, Vol. 69, 2110 (1972) and Gene, Vol. 17, 107 (1982), for instance.

Bacteria of the genus Bacillus can be transformed in accordance with the method described in Molecular and General Genetics, Vol. 168, 111 (1979), for instance.

Yeasts can be transformed in accordance with the method described in the Proceedings of the National Academy of Sciences of the USA, Vol. 75, 1929 (1978), for instance.

Insect cells can be transformed in accordance with the method described in Bio/Technology, 6, 47–55 (1988), for instance.

Animal cells can be transformed in accordance with the method described in Virology, Vol. 52, 456 (1973), for instance.

A transformant resulting from transformation with an expression vector containing DNA encoding the activin receptor protein is thus obtained.

For cultivating a transformant whose host is a bacterium of the genus Escherichia or Bacillus, it is appropriate to use a liquid medium supplemented with carbon sources, nitrogen sources, minerals and other substances necessary for the growth of the transformant. Example carbon sources include glucose, dextrin, soluble starch and sucrose. Example nitrogen sources include organic or inorganic substances such as ammonium salts, nitrates, corn steep liquor, peptone, casein, meat extract, soybean cake and potato extract. Example minerals include calcium chloride, sodium dihydrogen phosphate and magnesium chloride. Yeast extract, vitamins, growth promoters and other additives may be added. The pH of the medium is preferably about 5 to 8.

Examples of media preferably used to cultivate a bacterium of the genus Escherichia include the M9 medium containing glucose and casamino acid [Miller, Journal of Experiments in Molecular Genetics, 431–433, Cold Spring Harbor Laboratory, New York (1972)]. To increase promoter efficiency as necessary, a chemical agent such as 3β-indolyl acrylic acid may be added.

When the host is a bacterium of the genus Escherichia, cultivation is normally carried out at about 15 to 43° C. for about 3 to 24 hours, with aeration and/or stirring as necessary.

When the host is a bacterium of the genus Bacillus, cultivation is normally carried out at about 30 to 40° C. for about 6 to 24 hours, with aeration and/or stirring as necessary.

Examples of media for cultivating a transformant whose host is a yeast include Burkholder's minimal medium [Bostian, K. L. et al., Proceedings of the National Academy of Sciences of the USA, Vol. 77, 4505 (1980)] and SD medium containing 0.5% casamino acid [Bitter, G. A. et al., Proceedings of the National Academy of Sciences of the USA, Vol. 81, 5330 (1984)]. It is preferable to adjust the medium to a pH of about 5 to 8. Cultivation is normally carried out at about 20 to 35° C. for about 24 to 72 hours, with aeration and/or stirring as necessary.

Examples of media for cultivating a transformant whose host is an insect cell include Grace's insect medium [Grace, T. C. C., Nature, 195, 788 (1962)] supplemented with additives such as 10% inactivated bovine serum as appropriate. It is preferable to adjust the medium to a pH of about 6.2 to 6.4. Cultivation is normally carried out at about 27° C. for about 3 to 5 days, with aeration and/or stirring as necessary.

Examples of media for cultivating a transformant whose host is an animal cell include MEM medium containing about 5 to 20% fetal bovine serum [Science, Vol. 122, 501 (1952)], DMEM medium [Virology, Vol. 8, 396 (1959)], RPMI 1640 medium [The Journal of the American Medical Association, Vol. 199, 519 (1967)] and 199 medium [Proceeding of the Society for the Biological Medicine, Vol. 73, 1 (1950)]. The pH is preferably about 6 to 8. Cultivation is normally carried out at about 30 to 40° C. for about 15 to 60 hours, with aeration and/or stirring as necessary.

The receptor protein can be separated and purified from the above-described culture by, for example, the method described below.

For extracting the receptor protein from cultured cells, known methods can be used as appropriate, including the method in which cells are collected by a known method after cultivation, then suspended in an appropriate buffer, followed by cell disruption by ultrasonication, lysozyme treatment and/or freeze-thawing, after which a crude extract of receptor protein is obtained by centrifugation or filtration. The buffer may contain a protein denaturant such as urea or guanidine hydrochloride and/or a surfactant such as Triton X-100 (trade name).

When the receptor protein is secreted in the culture, the cells and supernatant are separated by a commonly known method and the latter is collected, after completion of cultivation. The receptor protein contained in the thus-obtained culture supernatant or extract can be purified by appropriate combinations of commonly known methods of separation and purification. Such known methods of separation and purification include those based on solubility differences, such as salting-out and solvent precipitation; those based mainly on molecular weight differences, such as dialysis, ultrafiltration, gel filtration and SDS-polyacrylamide gel electrophoresis; those based on charge differences, such as ion exchange chromatography; those based on specific affinity, such as affinity chromatography; those based on hydrophobicity differences, such as reverse-phase high performance liquid chromatography; and those based on isoelectric point differences, such as isoelectric focusing.

When the receptor protein is obtained in free form, it can be converted to an appropriate salt by a commonly known method or modification thereof; when the protein is obtained in salt form, it can be converted to free form by a commonly known method or modification thereof.

The receptor protein produced by a recombinant may be reacted with an appropriate protein-modifying enzyme before or after purification to modify the protein as desired or remove some polypeptides. Example protein-modifying enzymes include trypsin, chymotrypsin, arginine endopeptidase, protein kinase and glycosidase.

The activity of the resulting activin receptor protein can be determined by an experiment of binding to labeled ligand, an enzyme immunoassay using a specific antibody, etc.

The DNA encoding the receptor protein of the present invention and the receptor protein of the present invention can be used as reagent for various purposes, including ① determination of ligand against the receptor protein of the present invention, ② obtainment of antibodies and antisera, ③ construction of recombinant receptor protein expression systems, ④ development of receptor binding assay systems and screening for pharmaceutical candidate compounds using such expression systems, ⑤ drug designing based on comparison with structurally similar ligand receptors, and ⑥ reagent for preparation of probes and PCR primers for gene diagnosis, and ⑦ as a drug for gene therapy.

A receptor binding assay system using an expression system for the recombinant receptor protein of the present invention, in particular, makes it possible to screen for a receptor agonist or antagonist specific to warm-blooded animals, such as humans, which agonist or antagonist can be used as a prophylactic/therapeutic agent for various diseases.

Uses for the receptor protein of the present invention, salt thereof, DNA encoding said receptor protein, and antibodies against receptor proteins are hereinafter described specifically.

(1) Determination Method for Ligand Against the Receptor Protein of the Present Invention The receptor protein of the present invention or a salt thereof is useful as a reagent for searching or determining a ligand against the receptor protein of the present invention.

Accordingly, the present invention provides a determination method for a ligand against the receptor protein of the present invention characterized in that the receptor protein of the present invention or a salt thereof is brought into contact with a test compound.

Useful test compounds include known ligands (e.g., activin, inhibin, TGFβ, OP-1 gene product, Vg-1 gene product), and tissue extracts and cell culture supernatants of warm-blooded animals (e.g., mice, rats, pigs, bovines, sheep, monkeys, humans). For example, such a tissue extract, cell culture supernatant, or the like, may be added to the receptor protein of the present invention, followed by fractionation with monitoring of a cell-stimulating activity etc., to finally yield a single ligand.

Specifically, the ligand determination method of the present invention is carried out by using the receptor protein of the present invention or a salt thereof, or by constructing a recombinant receptor protein expression system and using a receptor binding assay system using said expression system, to determine a compound that binds to the receptor protein (e.g., peptides, proteins, non-peptide compounds, synthetic compounds, fermentation products) to exhibit a cell-stimulating activity (e.g., growth promotion, promotion or suppression of intracellular protein phosphorylation etc.) or a salt thereof.

The ligand determination method of the present invention is characterized by determining the amount of test compound bound, cell-stimulating activity, or the like, to the receptor protein of the present invention or a salt thereof when said receptor protein or a salt thereof is brought into contact with the test compound.

More specifically, the present invention provides:

① a method of determining a ligand against the receptor protein wherein the amount of labeled test compound bound to the receptor protein of the present invention or a salt thereof is determined when the labeled test compound is brought into contact with said protein or a salt thereof, ② a method of determining a ligand against the receptor protein wherein the amount of labeled test compound bound to cells containing the receptor protein of the present invention or the membrane fraction of said cells is determined when the labeled test compound is brought into contact with said cells or the membrane fraction thereof, ③ a method of determining a ligand against the receptor protein wherein the amount of labeled test compound bound to the receptor protein of the present invention is determined when the labeled test compound is brought into contact with said receptor protein as expressed on the cell membrane of a transformant containing DNA encoding the receptor protein of the present invention by culturing said transformant, ④ a method of determining a ligand against the receptor protein wherein a cell-stimulating activity via receptor protein (e.g., growth promotion, promotion or suppression of intracellular protein phosphorylation) is determined when a test compound is brought into contact with cells containing the receptor protein of the present invention, and ⑤ a method of determining a ligand against the receptor protein wherein a cell-stimulating activity via receptor protein (e.g., growth promotion, promotion or suppression of intracellular protein phosphorylation) is determined when a test compound is brought into contact with the receptor protein as expressed on the cell membrane of a transformant containing DNA encoding the receptor protein of the present invention by culturing said transformant.

The ligand determination method of the present invention is hereinafter described specifically.

First, although any subject can be used for the ligand determination method, as long as it contains the receptor protein of the present invention, i.e., a protein containing the amino acid sequence shown by SEQ ID NO:7, receptor proteins expressed in large amounts using animal cells are suitable for screening.

An receptor protein can be produced by the above-described method, specifically by expressing DNA encoding said protein in mammalian or insect cells. DNA fragments encoding the desired portion include, but are not limited to, cDNA. For example, gene fragments and synthetic DNA may also be used. For introducing a DNA fragment encoding an receptor protein into host animal cells and efficiently expressing it, it is preferable to insert said DNA fragment downstream from the polyhedrin promoter of nuclear polyhedrosis virus (NPV) which is a baculovirus having insect hosts, SV-40-derived promoter, retrovirus promoter, metallothionein promoter, human heat shock promoter, cytomegalovirus promoter, SRα promoter or the like. The amount and quality of receptor expressed can be determined by commonly known methods. For example, this determination can be achieved by the method described in the literature [Nambi, P. et al., The Journal of Biological Chemistry, Vol. 267, pp. 19555–19559 (1992)].

Accordingly, the subject containing a receptor protein or a partial peptide thereof for the ligand determination method of the present invention may be the receptor protein purified by a commonly known method, a partial peptide thereof, cells containing said protein, or the membrane fraction of cells containing said protein.

When cells containing the receptor protein are used for the ligand determination method of the present invention, said cells may be immobilized using glutaraldehyde, formalin etc. This immobilization can be achieved by a commonly known method.

Cells containing the receptor protein are host cells that have expressed the receptor protein, which host cells include *Escherichia coli* cells, *Bacillus subtilis* cells, yeast cells, insect cells and animal cells.

The membrane fraction is a fraction rich in cell membrane obtained by cell disruption and subsequent fractionation by a commonly known method. Useful cell disruption methods include cell squashing using a Potter-Elvehjem homogenizer, disruption using a Waring blender or Polytron (produced by Kinematica), ultrasonic disruption, and disruption by cell spraying via a thin nozzle under increased pressure using a French press or the like. Cell membrane fractionation is achieved mainly by centrifugal fractionation methods such as fractional centrifugation and density gradient centrifugation. For example, a cell disruption liquid is centrifuged at low rate (500 to 3,000 rpm) for a short period of time (normally about 1 to 10 minutes), the resulting supernatant is then centrifuged at a higher rate (15,000 to 30,000 rpm) normally for 30 minutes to 2 hours, to yield a precipitate as the membrane fraction. The membrane fraction thus obtained is rich in the activin receptor protein expressed and membrane components such as cell-derived phospholipids and membrane proteins.

The amount of receptor protein contained in cells containing the receptor protein or membrane fraction thereof is preferably $10^2$ to $10^8$ molecules per cell, more preferably $10^5$ to $10^7$ molecules. As the amount of expression increases, the ligand binding activity per unit of membrane fraction (specific activity) increases, enabling the construction of highly sensitive screening systems and assay of large amounts of samples of the same lot.

To perform methods ① through ③ above for determination of a ligand that binds to the receptor protein, an appropriate receptor fraction and a labeled test compound are necessary. The receptor fraction is preferably a natural receptor fraction or a recombinant receptor fraction possessing equivalent activity. Here, the term equivalent activity is intended to include ligand binding activity.

Useful labeled test compounds include activin, inhibin, TGFα, OP-1 gene product and Vg-1 gene product all labeled with [$^3$H], [$^{125}$I], [$^{14}$C], [$^{35}$S] or the like.

Specifically, to determine a ligand that binds to the receptor protein, a standard receptor preparation is first prepared by suspending cells containing the receptor protein or the membrane fraction thereof in a buffer appropriate for the determination. Any buffer can be used, as long as it does not interfere with ligand-receptor binding, such buffers including phosphate buffers or Tris-HCl buffers of pH about 4–10 (preferably pH about 6–8). For the purpose of reducing non-specific binding, surfactants such as CHAPS, Tween-80 (trade name) (produced by Kao-Atlas), digitonin and deoxycholate, and various proteins such as bovine serum albumin and gelatin, may be added to the buffer. Also, for the purpose of suppressing receptor and ligand decomposition by protease, protease inhibitors such as PMSF (phenylmethanesulfonyl fluoride), leupeptin, E-64 (produced by Peptide Institute, Inc.) and pepstatin may be added. To 0.01–10 ml of said receptor solution, a test compound labeled with a given amount (5,000 to 500,000 cpm) of [$^3$H], [$^{125}$I], [$^{14}$C] or the like is added. To determine the amount of non-specific binding (NSB), a reaction tube containing an unlabeled test compound in excess is also provided. Reaction is carried out at 0 to 50° C., preferably 4 to 37° C. for 20 minutes to 24 hours, preferably 30 minutes to 3 hours. After completion of the reaction, the reaction mixture is filtered through glass fiber filter paper etc. and washed with an appropriate amount of the same buffer, after which the residual radioactivity in the glass fiber filter paper is measured using a liquid scintillation counter or γ-counter. A test compound exceeding 0 cpm in count (B−NSB) obtained by subtracting nonspecific binding (NSB) from total binding (B) may be selected as a ligand against the activin receptor protein of the present invention.

To perform method ④ or ⑤ above for determination of a ligand against the receptor protein, a cell-stimulating activity via receptor protein (e.g., growth promotion, promotion or suppression of intracellular protein phosphorylation) may be determined using a known method or a commercially available assay kit. Specifically, cells containing the receptor protein are first cultured on multiwell plates etc. Prior to ligand determination, the medium is replaced with fresh medium or an appropriate non-cytotoxic buffer, followed by incubation in the presence of a test compound etc. for a given period of time, after which cells are extracted or the supernatant is recovered and the resulting product is quantified as appropriate. When it is difficult to detect the production of the cell-stimulating activity index substance (e.g., plasminogen activator inhibitor 1, fibronectin) due to a decomposing enzyme contained in the cells, an inhibitor against said decomposing enzyme may be added before assay.

The kit of the present invention for determination of a ligand that binds to the receptor protein of the present invention comprises the receptor protein of the present invention or a salt thereof, cells containing the receptor protein of the present invention, or the membrane fraction thereof.

Some examples of the ligand determination kit of the present invention are given below.

1. Ligand Determination Reagents
① Assay Buffer and Washing Buffer
Hanks' balanced salt solution (produced by GIBCO) supplemented with 0.05% bovine serum albumin (produced by Sigma Corporation).

After being sterilized by filtration through a filter of 0.45 μm in pore size, this buffer may be stored at 4° C., or may be prepared freshly at each use.
② Standard Activin Receptor Protein Preparation
CHO cells containing a receptor protein expressed therein are subcultured at 5×10$^5$ cells/well on 12-well plates at 37° C. in the presence of 5% $CO_2$ and 95% air for 2 days.
③ Labeled Test Compound
Compound labeled with commercially available [$^3$H], [$^{125}$I], [$^{14}$C], [$^{35}$S] or the like, or compound labeled by an appropriate method.

The labeled test compound in aqueous solution is stored at 4° C. or −20° C., and diluted to 1 μM with the assay buffer before use. When the test compound is practically insoluble in water, it must be dissolved in dimethylformamide, DMSO, methanol, or the like.
④ Standard Liquid Solution
The labeled compound obtained in term ③ above is diluted to 1 mM with PBS containing 0.1% bovine serum albumin (produced by Sigma Corporation).
2. Method of Assay
① After CHO cells containing a receptor protein expressed therein, cultured on 12-well tissue culture plates, are twice washed with 1 ml of the assay buffer, 490 μl of the assay buffer is added to each well.
② Five microliter of the labeled test compound is added, followed by reaction at room temperature for 1 hour. To determine the amount of non-specific binding, 5 μl of the unlabeled test compound is added before reaction.
③ After the reaction mixture is removed, the plate is washed 3 times with 1 ml of the washing buffer. The labeled test compound bound to cells is dissolved in 0.2 N NaOH-1% SDS and mixed with 4 ml of liquid scintillator A (produced by Wako Pure Chemical Industries).
④ Radioactivity is determined using a liquid scintillation counter (produced by Beckman).
(2) Prophylactic/Therapeutic Agent for Deficiency of the Receptor Protein of the Present Invention If a ligand against the receptor protein of the present invention is demonstrated by method (1) above, DNA encoding the receptor protein of the present invention could be used as a prophylactic/therapeutic agent against activin receptor protein deficiency according to the action of said ligand.

For example, for a patient in whom the physiological action of ligand is not expected due to decreased content of the receptor protein of the present invention in the body, the receptor protein content in the patient can be increased to ensure satisfactory ligand action by, for example, (a) administering DNA encoding the receptor protein of the present invention to the patient and expressing the receptor protein in the body, or (b) inserting DNA encoding the receptor protein of the present invention to brain cells etc., and expressing it there, then transplanting the brain cells etc. to the patient. DNA encoding the receptor protein of the present invention can therefore be used as a safe prophylactic/therapeutic agent for activin receptor protein deficiency of low toxicity.

When the DNA of the present invention is used as a prophylactic/therapeutic agent as described above, the DNA may be used as such or after being inserted to an appropriate vector such as the retrovirus vector, adenovirus vector or adenovirus-associated virus vector, followed by a conventional method of drug administration. For example, the DNA can be used orally in the form of tablets, capsules, elixirs, microcapsules etc., all of which may be sugar coated as necessary, or non-orally in the form of injectable preparations such as aseptic solutions and suspensions in water or other pharmaceutically acceptable liquids. These preparations can be produced by mixing the DNA of the present invention with physiologically acceptable carriers, flavoring agents, excipients, vehicles, antiseptics, stabilizers, binders etc. in unit dosage forms for generally accepted manners of pharmaceutical making. Active ingredient contents in these preparations are set so that an appropriate dose within the specified range is obtained.

Additives which can be mixed in tablets, capsules etc. include binders such as gelatin, corn starch, tragacanth and gum arabic, excipients such as crystalline cellulose, swelling agents such as corn starch, gelatin and alginic acid, lubricants such as magnesium stearate, sweetening agents such as sucrose, lactose and saccharin, and flavoring agents such as peppermint and cherry. When the unit dosage form is the capsule, the above-mentioned materials may further incorporate liquid carriers such as oils and fats. Sterile compositions for injection can be formulated by ordinary methods of pharmaceutical making such as by dissolving or suspending active ingredients, naturally occurring vegetable oils such as sesame oil and coconut oil, etc. in vehicles such as water for injection. Aqueous liquids for injection include physiological saline and isotonic solutions containing glucose and other auxiliary agents (e.g., D-sorbitol, D-mannitol, sodium chloride), and may be used in combination with appropriate dissolution aids such as alcohols (e.g., ethanol), polyalcohols (e.g., propylene glycol, polyethylene glycol), nonionic surfactants (e.g., polysorbate 80 (trade name), HCO-50) etc. Oily liquids include sesame oil and soybean oil, and may be used in combination with dissolution aids such as benzyl benzoate and benzyl alcohol.

The aqueous liquid may also be formulated with buffers (e.g., phosphate buffer, sodium acetate buffer), soothing agents (e.g., benzalkonium chloride, procaine hydrochloride), stabilizers (e.g., human serum albumin, polyethylene glycol), preservatives (e.g., benzyl alcohol, phenol), antioxidants etc. The thus-prepared injectable liquid is normally filled in an appropriate ampule. Because the thus-obtained preparation is safe and of low toxicity, it can be administered to warm-blooded mammals (e.g., rats, rabbits, sheep, pigs, bovines, cats, dogs, monkeys, humans), for instance. The dose of said DNA is normally about 0.1 to 100 mg, preferably about 1.0 to 50 mg, and more preferably about 1.0 to 20 mg per day for an adult (weighing 60 kg) in oral administration, depending on symptoms etc. In non-oral administration, it is advantageous to administer the DNA in the form of injectable preparation at a daily dose of about 0.01 to 30 mg, preferably about 0.1 to 20 mg, and more preferably about 0.1 to 10 mg per administration for an adult (weighing 60 kg), depending on subject of administration, target organ, symptoms, method of administration etc. For other animal species, corresponding doses as converted per 60 kg weight can be administered.

(3) Quantitative Determination Method for Ligand Against the Receptor Protein of the Present Invention The receptor protein of the present invention or a salt thereof enables highly sensitive quantitative determination of ligand concentration in the body because it is capable of binding to ligand.

The quantitative determination method of the present invention can be used in combination with competitive assay, for example. In other words, the ligand concentration in the sample can be determined by bringing it into contact with the receptor protein of the present invention or a salt thereof. Specifically, it can be performed by the methods described in references ① and ② below or modifications thereof.

① Hiroshi Irie ed., Radioimmunoassay, Kodansha, 1974.
② Hiroshi Irie ed., Zoku Radioimmunoassay, Kodansha, 1979.

(4) Screening Method for Compounds That Inhibit or Promote the Binding of the Receptor Protein of the Present Invention and Ligand By using the receptor protein of the present invention or a salt thereof, or by constructing an recombinant receptor protein expression system and using a receptor binding assay system using said expression system, it is possible to screen for a compound that inhibits or promotes the binding of a ligand and the receptor protein (e.g., peptides, proteins, non-peptide compounds, synthetic compounds, fermentation products) or for a salt thereof. Such compounds include compounds that exhibit a cell-stimulating activity via receptor (e.g., growth promotion, promotion or suppression of intracellular protein phosphorylation), and compounds lacking said cell-stimulating activity (what is called receptor antagonists of the present invention).

Accordingly, the present invent-on provides a method of screening for a compound that inhibits or promotes the binding of a ligand and the receptor protein of the present invention or a salt thereof, wherein comparison is made between case (i) in which the ligand is brought into contact with the receptor protein of the present invention or a salt thereof, and case (ii) in which both the ligand and a test compound are brought into contact with the receptor protein of the present invention or a salt thereof.

The screening method of the present invention is characterized by comparison of, for example, the amount of ligand bound to the receptor protein of the present invention or a salt thereof, or cell-stimulating activity, between case (i) in which the ligand is brought into contact with the receptor protein of the present invention or a salt thereof, and case (ii) in which both the ligand and a test compound are brought into contact with the receptor protein of the present invention or a salt thereof.

More specifically, the present invention provides:

① a method of screening for a compound that inhibits or promotes the binding of a ligand and the receptor protein of the present invention or a salt thereof, or for a salt thereof, wherein the amount of labeled ligand bound to said protein or a salt thereof, is compared between a case in which the labeled ligand is brought into contact with the receptor protein of the present invention or a salt thereof, and another case in which both the labeled ligand and a test compound are brought into contact with the receptor protein of the present invention or a salt thereof, ② a method of screening for a compound that inhibits or promotes the binding of a ligand and the receptor protein of the present invention, or for a salt thereof, wherein the amount of labeled ligand bound to cells containing the receptor protein of the present invention is compared between a case in which the labeled ligand is brought into contact with said cells or the membrane fraction thereof and another case in which both the labeled ligand and a test compound are brought into contact with said cells or the membrane fraction thereof, ③ a method of screening for a compound that inhibits or promotes the binding of a ligand and the receptor protein of the present invention, or for a salt thereof, wherein the amount of labeled ligand bound to said receptor protein is compared between a case in which the labeled ligand is brought into contact with said receptor protein as expressed on the cell membrane of a transformant containing DNA encoding the receptor protein of the present invention by culturing said transformant, and another case in which both the labeled ligand and a test compound are brought into contact with said receptor protein as expressed on the cell membrane of a transformant containing DNA encoding the receptor protein of the present invention by culturing said transformant, ④ a method of screening for a compound that inhibits or promotes the binding of a ligand and the activin receptor protein of the present invention, or for a salt thereof, wherein a cell-stimulating activity via activin receptor protein (e.g., growth promotion, promotion or suppression of intracellular protein phosphorylation) is compared between a case in which a compound that activates the receptor protein of the present invention (e.g., ligand against the receptor protein of the present invention) is brought into contact with cells containing the receptor protein of the present invention, and another case in which both the compound that activates the receptor of the present invention and a test compound are brought into contact with cells containing the receptor protein of the present invention, and ⑤ a method of screening for a compound that inhibits or promotes the binding of a ligand and he activin receptor protein of the present invention, or for a salt thereof, wherein a cell-stimulating activity via receptor (e.g., growth promotion, promotion or suppression of intracellular protein phosphorylation) is compared between a case in which a compound that activates the receptor of the present invention (e.g., ligand against the activin receptor protein of the present invention) is brought into contact with the receptor protein as expressed on the cell membrane of a transformant containing DNA encoding the receptor protein of the present invention by culturing said transformant, and another case in which both the compound that activates the receptor protein of the present invention and a test compound are brought into contact with the receptor protein as expressed on the cell membrane of a transformant containing DNA encoding the receptor protein of the present invention by culturing said transformant.

The screening method of the present invention is hereinafter described specifically.

First, although any subject can be used for the screening method of the present invention, as long as it contains the receptor protein of the present invention or a salt thereof, preference is given to membrane fractions of organs of warm-blooded animals. Because human organs are very difficult to obtain, however, receptor proteins expressed in large amounts using recombinants are suitable for screening.

A receptor protein can be produced by the above-described method, specifically by expressing DNA encoding said protein in mammalian or insect cells. DNA fragments encoding the desired portion include, but are not limited to, complementary DNA. For example, gene fragments and synthetic DNA may also be used. For introducing a DNA fragment encoding a receptor protein into host animal cells and efficiently expressing it, it is preferable to insert said DNA fragment downstream from the polyhedrin promoter of nuclear polyhedrosis virus (NPV) which is a baculovirus having insect hosts, SV-40-derived promoter, retrovirus promoter, metallothionein promoter, human heat shock promoter, cytomegalovirus promoter, SRα promoter or the like. The amount and quality of receptor expressed can be determined by commonly known methods. For example, this determination can be achieved by the method described in the literature [Nambi, P. et al., The Journal of Biological Chemistry, Vol. 267, pp. 19555–19559 (1992)].

Accordingly, the subject containing a receptor protein or a salt thereof for the screening method of the present invention may be a receptor protein purified by a commonly known method, cells containing said protein, or the membrane fraction of cells containing said protein.

When cells containing a receptor protein are used for the screening method of the present invention, said cells may be immobilized using glutaraldehyde, formalin etc. This immobilization can be achieved by a commonly known method.

Cells containing a receptor protein are host cells that have expressed the receptor protein, which host cells include *Escherichia coli* cells, *Bacillus subtilis* cells, yeast cells, insect cells and animal cells.

The membrane fraction is a fraction rich in cell membrane obtained by cell disruption and subsequent fractionation by a commonly known method. Useful cell disruption methods include cell squashing using a Potter-Elvehjem homogenizer, disruption using a Waring blender or Polytron (produced by Kinematica), ultrasonic disruption, and disruption by cell spraying via a thin nozzle under increased pressure using a French press or the like. Cell membrane fractionation is achieved mainly by centrifugal fractionation methods such as fractional centrifugation and density gradient centrifugation. For example, a cell disruption liquid is centrifuged at low rate (500 to 3,000 rpm) for a short period of time (normally about 1 to 10 minutes), the resulting supernatant is then centrifuged at higher rate (15,000 to 30,000 rpm) normally for 30 minutes to 2 hours, to yield a precipitate as the membrane fraction. The membrane fraction thus obtained is rich in the receptor protein expressed and membrane components such as cell-derived phospholipids and membrane proteins.

The amount of receptor protein contained in cells containing the receptor protein or membrane fraction thereof is preferably $10^2$ to $10^8$ molecules per cell, more preferably $10^5$ to $10^7$ molecules. As the amount of expression increases, the ligand binding activity per unit of membrane fraction (specific activity) increases, enabling the construction of highly sensitive screening systems and assay of large amounts of samples of the same lot.

To perform screening methods ① through ③ above for a compound that inhibits the binding of a ligand and the receptor protein of the present invention, an appropriate receptor fraction and a labeled ligand are necessary. The receptor fraction is preferably a natural receptor fraction or a recombinant receptor fraction possessing equivalent activity. Here, the term equivalent activity is intended to include ligand binding activity.

Useful labeled ligands include labeled ligands and labeled ligand analog compounds, such as those labeled with [$^3$H], [$^{125}$I], [$^{14}$C], [$^{35}$S] or the like.

Specifically, to screen for a compound that inhibits the binding of a ligand and a receptor protein, a standard receptor preparation is first prepared by suspending cells containing the receptor protein or the membrane fraction thereof in a buffer appropriate for the screening. Any buffer can be used, as long as it does not interfere with ligand-receptor binding, such buffers including phosphate buffers and Tris-HCl buffers of pH about 4–10 (preferably pH about 6–8). For the purpose of reducing non-specific binding, surfactants such as CHAPS, Tween80 (trade name)

(produced by Kao-Atlas), digitonin and deoxycholate may be added to the buffer. Also, for the purpose of suppressing receptor and ligand decomposition by protease, protease inhibitors such as PMSF, leupeptin, E-64 (produced by Peptide Institute, Inc.) and pepstatin may be added. To 0.01–10 ml of said receptor solution, a ligand labeled with a given amount (5,000 to 500,000 cpm) of marker is added. Also added is a test compound at $10^{-4}$ M to $10^{-10}$ M. To determine the amount of non-specific binding (NSB), a reaction tube containing an unlabeled ligand in excess is also provided. Reaction is carried out at 0 to 50° C., preferably 4 to 37° C. for 20 minutes to 24 hours, preferably 30 minutes to 3 hours. After completion of the reaction, the reaction mixture is filtered through glass fiber filter paper etc. and washed with an appropriate amount of the same buffer, after which the residual radioactivity in the glass fiber filter paper is measured using a liquid scintillation counter or γ-counter. A test compound not higher than 50%, for instance, in amount of specific binding (B−NSB), relative to the count obtained by subtracting nonspecific binding (NSB) from the count in the absence of antagonists (B0) (B0−NSB), may be selected as a candidate substance having potential for antagonism; a test compound not lower than 150%, for instance, in amount of specific binding (B−NSB), may be selected as a candidate substance having potential for promotion of binding.

To perform screening method ④ or ③ above for a compound that inhibits or promotes the binding of a ligand and the receptor protein of the present invention, a cell-stimulating activity via receptor protein (e.g., growth promotion, promotion or suppression of intracellular protein phosphorylation) may be determined using a known method or a commercially available assay kit. Specifically, cells containing the receptor protein are first cultured on multi-well plates etc. Prior to screening, the medium is replaced with fresh medium or an appropriate non-cytotoxic buffer, followed by incubation in the presence of a test compound etc. for a given period of time, after which cells are extracted or the supernatant is recovered, and the resulting product is quantified as appropriate. When it is difficult to detect the production of the cell-stimulating activity index substance (e.g., plasminogen activator inhibitor 1, fibronectin) due to a decomposing enzyme contained in the cells, an inhibitor against said decomposing enzyme may be added before assay.

For screening based on cell-stimulating activity determination, cells containing an appropriate receptor protein expressed therein are necessary. Preferable cells containing the receptor protein of the present invention expressed therein include a cell line having the receptor protein of the present invention in natural form (e.g., mouse embryonic tumor cell line P19) and a cell line that expresses a recombinant receptor protein.

Useful test compounds include peptides, proteins, non-peptide compounds, synthetic compounds, fermentation products, cell extract, plant extract and animal tissue extract, and may be new compounds or known compounds.

The screening kit for a compound that inhibits or promotes the binding of a ligand and the receptor protein of the present invention or a salt thereof comprises the receptor protein of the present invention or a salt thereof, a partial peptide thereof, or a salt thereof, cells containing the receptor protein of the present invention, or the membrane fraction thereof.

Some examples of the screening kit of the present invention are given below.

1. Screening Reagents
① Assay Buffer and Washing Buffer
Hanks' balanced salt solution (produced by GIBCO) supplemented with 0.05% bovine serum albumin (produced by Sigma Corporation)
After being sterilized by filtration through a filter of 0.45 μm in pore size, this buffer may be stored at 4° C., or may be prepared freshly at each use.
② Standard Receptor Protein Preparation
CHO cells containing a receptor protein expressed therein are subcultured at $5 \times 10^5$ cells/well on 12-well plates at 37° C. in the presence of 5% $CO_2$ and 95% air for 2 days.at 4° C. or −20° C., and diluted to 1 μM with the assay buffer before use.
③ Labeled Ligand
Aqueous ligand solution labeled with commercially available [$^3$H], [$^{125}$I], [$^{14}$C], [$^{35}$S] or the like is stored.
④ Standard Ligand Solution
The ligand is dissolved to 1 mM in PBS containing 0.1% bovine serum albumin (produced by Sigma Corporation) and stored at −20° C.
2. Method of Assay
① After CHO cells containing a receptor protein expressed therein, cultured on 12-well tissue culture plates, are twice washed with 1 ml of the assay buffer, 490 μl of the assay buffer is added to each well.
② After 5 μl of the test compound is added at $10^{-3}$ to $10^{-10}$ M, 5 μl of the labeled ligand is added, followed by reaction at room temperature for 1 hour. To determine the amount of non-specific binding, 5 μl of the unlabeled ligand at $10^{-3}$ M, in place of the test compound, is added before reaction.
③ After the reaction mixture is removed, the plate is washed 3 times with 1 ml of the washing buffer. The labeled ligand bound to cells is dissolved in 0.2 N NaOH-1% SDS and mixed with 4 ml of liquid scintillator A (produced by Wako Pure Chemical Industries).
④ Radioactivity is determined using a liquid scintillation counter (produced by Beckman). Percent maximum binding (PMB) is calculated using equation 1 below.
Equation 1
PMB=[(B−NSB)/(B0−NSB)]×100
PMB: Percent maximum binding
B: Value obtained in presence of sample
NSB: Non-specific binding
B0: Maximum binding The compound or salt thereof obtained using the screening method or screening kit of the present invention is a compound that inhibits or promotes the binding of a ligand and the receptor of the present invention, specifically a compound possessing a cell-stimulating activity via receptor or salt thereof (what is called activin receptor agonist) or a compound not possessing such cell-stimulating activity (what is called activin receptor antagonist). Useful test compounds include peptides, proteins, non-peptide compounds, synthetic compounds and fermentation products, and may be new compounds or known compounds.

Because said receptor agonist processes the same bioactivity as that of the ligand against the receptor protein of the present invention, it is useful as a safe pharmaceutical composition of low toxicity, especially a prophylactic/therapeutic agent for nerve degeneration disease, according to said ligand activity.

Conversely, because said receptor antagonists are capable of suppressing the bioactivity of a ligand against the receptor protein of the present invention, they are useful as safe pharmaceutical compositions of low toxicity, especially prophylactic/therapeutic agents for nerve degeneration disease, in suppressing said ligand bioactivity.

When the compound obtained using the screening method or screening kit of the present invention or a salt thereof is used as a pharmaceutical composition as described above, it can be used safely at low toxicity by conventional methods. For example, it can be used orally in the form of tablets, capsules, elixirs, microcapsules etc., all of which may be sugar coated as necessary, or non-orally in the form of injectable preparations such as aseptic solutions and suspensions in water or other pharmaceutically acceptable liquids. These preparations can be produced by mixing the compound or salt thereof with physiologically acceptable carriers, flavoring agents, excipients, vehicles, antiseptics, stabilizers, binders etc. in unit dosage forms for generally accepted manners of pharmaceutical making. Active ingredient contents in these preparations are set so that an appropriate dose within the specified range is obtained.

Additives which can be mixed in tablets, capsules etc. include binders such as gelatin, corn starch, tragacanth and gum arabic, excipients such as crystalline cellulose, swelling agents such as corn starch, gelatin and alginic acid, lubricants such as magnesium stearate, sweetening agents such as sucrose, lactose and saccharin, and flavoring agents such as peppermint and cherry. When the unit dosage form is the capsule, the above-mentioned materials may further incorporate liquid carriers such as oils and fats. Sterile compositions for injection can be formulated by ordinary methods of pharmaceutical making such as by dissolving or suspending active ingredients, naturally occurring vegetable oils such as sesame oil and coconut oil, etc. in vehicles such as water for injection.

Aqueous liquids for injection include physiological saline and isotonic solutions containing glucose and other auxiliary agents (e.g., D-sorbitol, D-mannitol, sodium chloride), and may be used in combination with appropriate dissolution aids such as alcohols (e.g., ethanol), polyalcohols (e.g., propylene glycol, polyethylene glycol), nonionic surfactants (e.g., polysorbate 80 (trade name), HCO-50) etc. Oily liquids include sesame oil and soybean oil, and may be used in combination with dissolution aids such as benzyl benzoate and benzyl alcohol. The aqueous liquid may also be formulated with buffers (e.g., phosphate buffer, sodium acetate buffer), soothing agents (e.g., benzalkonium chloride, procaine hydrochloride), stabilizers (e.g., human serum albumin, polyethylene glycol), preservatives (e.g., benzyl alcohol, phenol), antioxidants etc. The thus-prepared injectable liquid is normally filled in an appropriate ampule. Because the thus-obtained preparation is safe and of low toxicity, it can be administered to warm-blooded mammals (e.g., rats, rabbits, sheep, pigs, bovines, cats, dogs, monkeys, humans), for instance.

The dose of said compound or a salt thereof is normally about 0.1 to 100 mg, preferably about 1.0 to 50 mg, and more preferably about 1.0 to 20 mg per day for an adult (weighing 60 kg) in oral administration, depending on symptoms etc. In non-oral administration, it is advantageous to administer the compound or a salt thereof in the form of injectable preparation at a daily dose of about 0.01 to 30 mg, preferably about 0.1 to 20 mg, and more preferably about 0.1 to 10 mg per administration for an adult (weighing 60 kg), depending on subject of administration, target organ, symptoms, method of administration etc. For other animal species, corresponding doses as converted per 60 kg weight can be administered.

(5) Production of Antibody or Antiserum Against the Receptor Protein of the Present Invention, Partial Peptide Thereof, or Salt Thereof An antibody (e.g., polyclonal antibody, monoclonal antibody) or antiserum against the receptor protein of the present invention or a salt thereof, can be produced by a commonly known method of antibody or antiserum production using the receptor protein of the present invention or a salt thereof as an antigen. For example, a monoclonal antibody can be produced by the method described below.

Preparation of Monoclonal Antibody (a) Preparation of Monoclonal Antibody Producer Cells The receptor protein of the present invention, a partial peptide thereof, or a salt thereof (hereinafter also referred to as activin receptor) is administered to warm-blooded animals at a site permitting antibody production by its administration, as such or in combination with a carrier, diluent etc. To increase antibody productivity, Freund's complete or incomplete adjuvant may be administered. Administration is normally performed about 2 to 10 times in total once every 2 to 6 weeks.

Although useful warm-blooded animals include monkeys, rabbits, dogs, guinea pigs, mice, rats, sheep, goat and chickens, mice and rats are preferred.

For preparing monoclonal antibody producer cells, animals showing an antibody titer are selected from antigen-immunized warm-blooded animals, e.g., mice; 2 to 5 days after final immunization, spleens or lymph nodes are collected; the antibody-producing cells contained therein are fused with myeloma cells to yield a monoclonal antibody producer hybridoma. Antibody titer in the antiserum is determined by reacting a labeled receptor as described below and the antiserum, then determining the activity of marker bound to the antibody. Fusion can be achieved by a known method such as the method of Kohler and Milstein [Nature, 256, 495 (1975)]. Although useful fusogens include polyethylene glycol (PEG) and Sendai virus, PEG is preferred.

Although useful myeloma cell lines include NS-1, P3U1, SP2/0 and AP-1, P3U1 is preferred. The number ratio of antibody-producing cells (splenocytes) and myeloma cells used is preferably about 1:1 to 20:1; cell fusion is facilitated when incubation is conducted at 20–40° C., preferably 30–37° C. for 1 to 10 minutes in the presence of about 10–80% PEG (preferably PEG1000 to PEG6000).

Although various methods are applicable to screening for hybridomas that produce an anti-activin receptor antibody, including the method in which a hybridoma culture supernatant is added to a solid phase (e.g., microplate) to which a receptor antigen is previously adsorbed directly or via a carrier, after which an anti-immunoglobulin antibody (anti-mouse immunoglobulin antibody in the case of mouse cells for cell fusion) or protein A labeled with a radioactive substance, enzyme or the like is added to detect the anti receptor monoclonal antibody bound to the solid phase, and the method in which a hybridoma culture supernatant is added to a solid phase to which an anti-immunoglobulin antibody or protein A is previously adsorbed, after which a receptor labeled with a radioactive substance, enzyme or the like is added to detect the anti receptor monoclonal antibody bound to the solid phase.

Selection of anti receptor monoclonal antibodies can be achieved by a commonly known method or modification thereof, normally in an animal cell culture medium supplemented with HAT (hypoxanthine, aminopterin, thymidine). Any selection and breeding media can be used, as long as they allow the hybridoma to grow. Useful media include RPMI 1640 medium containing 1–20%, preferably 10–20% fetal calf serum, GIT medium containing 1–10% fetal calf serum (Wako Pure Chemical Industries) and serum-free medium for hybridoma culture (SFM-101, Nissui Pharmaceutical). Culturing temperature is normally 20–40° C., preferably about 37° C. Culturing time is normally 5 days to 3 weeks, preferably 1 to 2 weeks. Cultivation is normally carried out in the presence of 5% gaseous carbon dioxide. Antibody titer of the hybridoma culture supernatant can be determined in the same manner as for the anti receptor antibody titer in the antiserum.

(b) Purification of Monoclonal Antibody

An anti receptor monoclonal antibody can be separated and purified by methods of immunoglobulin separation and purification [e.g., salting-out, alcohol precipitation, isoelectric precipitation, electrophoresis, adsorption/desorption using ion exchanger (e.g., DEAE), ultracentrifugation, gel filtration, and specific purification in which the desired antibody alone is collected using an active adsorbent such as antigen-bound solid phase, protein A, protein G or the like, followed by breaking the bond], as in ordinary separation and purification of polyclonal antibodies.

Because the receptor antibody of the present invention as produced by method (a) or (b) above is capable of specifically recognizing the receptor, it can be used to quantify a receptor in the subject solution, especially by sandwich immunometry etc.

Accordingly, the present invention provides, for example:

(i) a method of quantifying a receptor in a subject solution wherein an antibody reactive with the receptor of the present invention, the subject solution, and a labeled receptor are competitively reacted together, and the ratio of labeled receptor bound to the antibody is determined, and (ii) a method of quantifying a receptor in a subject solution by simultaneously or sequentially reacting the subject solution, an antibody insolubilized on a carrier and a labeled antibody, and determining the activity of the marker on the insolubilizing carrier, wherein one antibody recognizes the N- or C-terminal portion of the receptor and the other is reactive with the amino acid sequence of SEQ ID NO:7.

The monoclonal antibody of the present invention, which recognizes a receptor (hereinafter also referred to as anti receptor antibody) can be used not only to measure the receptor but also to detect the receptor by tissue staining etc. For these purposes, the antibody molecular may be used as such or as the $F(ab')_2$, Fab' or Fab fraction thereof. When using the antibody of the present invention, any assay method can be employed, as long as the amount of antibody, antigen or antibody-antigen complex corresponding to the amount of antigen (e.g., amount of activin receptor) in the subject solution is chemically or physically detected and calculated on a standard curve drawn using a standard solution containing a known amount of antigen. Although useful assay methods include nephrometry, competitive assay, immunometry and the sandwich method, the sandwich method described below is particularly preferable in terms of sensitivity and specificity.

Markers which can be used for assay methods using a labeled substance include radioisotopes, enzymes, fluorescent substances and luminescent substances. Preferable radioisotopes include [$^{125}$I], [$^{131}$I], [$^{3}$H] and [$^{14}$C]. Such enzymes are preferably stable and of high specific activity, exemplified by β-galactosidase, β-glucosidase, alkaline phosphatase, peroxidase and malic acid dehydrogenase. Useful fluorescent substances include fluorescamine and fluorescein isothiocyanate. Useful luminescent substances include luminol, luminol derivatives, luciferin and Lucigenin. Also, biotin-avidin systems can be used to bind an antibody or antigen and a marker.

Antigen or antibody insolubilization may be achieved using physical adsorption or by a commonly used method based on chemical bonds for insolubilization and immobilization of proteins, enzymes etc. Useful carriers include insoluble polysaccharides such as agarose, dextran and cellulose, synthetic resins such as polystyrene, polyacrylamide and silicone, and glass. In the sandwich method, a subject solution is reacted with an insolubilized anti receptor antibody (primary reaction), followed by another reaction of a labeled anti receptor antibody (secondary reaction), after which the activity of marker on the insolubilizing carrier is determined to obtain the amount of receptor in the subject solution. The primary and secondary reactions may be carried out in the reverse order, simultaneously, or at a time interval. The marker and insolubilization method used may be the same as those described above. In immunometry by the sandwich method, solid phase antibodies or marker antibodies need not be used singly; they may be used in a mixture of two or more such antibodies to improve assay sensitivity or for other purposes.

In the assay method for receptor by the sandwich method of the present invention, the anti receptor antibodies used in the primary and secondary reactions are preferably antibodies having mutually different receptor binding sites. In other words, when the antibody for the secondary reaction recognizes the C- or N-terminal portion of the receptor, the antibody for the primary reaction preferably recognizes the amino acid sequence shown by SEQ ID NO:7.

The receptor antibody of the present invention can be used for assay systems other than those based on the sandwich method, such as competitive assay, immunometry or nephrometry. In competitive assay, an antigen and labeled antigen in a subject solution are competitively reacted with an antibody, after which the unreacted labeled antigen (F) and antibody-bound labeled antigen (B) are separated (B/F separation), the amount of marker activity in either B or F is then determined to obtain the amount of antigen in the subject solution. This reaction employs either the liquid phase method using a soluble antibody and using polyethylene glycol, a secondary antibody against the above antibody etc. for B/F separation, or the solid phase method using a primary antibody immobilized on a solid phase, or using a soluble primary antibody and a secondary antibody immobilized on a solid phase.

In immunometry, an antigen and immobilized antigen on solid phase in the subject solution are competitively reacted with a given amount of labeled antibody, followed by separation of the solid and liquid phases, or the antigen in the subject solution is reacted with an excess of labeled antibody, then an immobilized antigen on solid phase is added to bind the unreacted labeled antibody to the solid phase, followed by separation of the solid and liquid phases. The amount of marker activity in either phase is then determined to obtain the amount of antigen in the subject solution.

In nephrometry, the amount of insoluble precipitate resulting from antigen-antibody reaction in gel or solution is determined. Even when the amount of antigen in the subject solution is so small that only a small amount of precipitate is obtained, laser nephrometry, based on laser scattering, etc. is preferably used.

In applying these immunological assays to the assay method of the present invention, there is no need for special conditions, procedures etc. A receptor assay system may be constructed on the basis of ordinary conditions, procedures etc. for respective methods, in consideration of ordinary technical aspects known to those skilled in the art. For details of these common technical approaches, published overviews, books etc. may serve as references [see e.g., "Radioimmunoassay," Hiroshi Irie ed., Kodansha, 1974, "Zoku Radioimmunoassay," Hiroshi Irie ed., Kodansha, 1979, "Koso Meneki Sokuteihou," Eiji Ishikawa et al. ed., Igaku-Shoin Ltd., 1978, "Koso Meneki Sokuteihou," 2nd edition, Eiji Ishikawa et al. ed., Igaku-Shoin Ltd., 1982, "Koso Meneki Sokuteihou," 3rd edition, Eiji Ishikawa et al. ed., Igaku-Shoin Ltd., 1987, "Methods in Enzymology," Vol. 70 (Immunochemical Techniques, Part A), ibid., Vol. 73 (Immunochemical Techniques, Part B), ibid., Vol. 74 (Immunochemical Techniques, Part C), ibid., Vol. 84 (Immunochemical Techniques, Part D: Selected Immunoassays), ibid., Vol. 92 (Immunochemical Techniques, Part E: Monoclonal Antibodies and General Immunoassay Methods), ibid., Vol. 121 (Immunochemical Techniques, Part I: Hybridoma Technology and Monoclonal Antibodies), all published by Academic Press].

The receptors can be quantified at high sensitivity using the receptor antibody of the present invention as described above.

Abbreviations for bases, amino acids and others used in the present specification and attached drawings are based on abbreviations specified by the IUPAC-IUB Commission on Biochemical Nomenclature or abbreviations in common use in relevant fields. Some examples are given below. When an optical isomer may be present in amino acid, it is of the L-configuration, unless otherwise stated.

DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetraacetic acid
SDS: Sodium dodecyl sulfate
EIA: Enzyme immunoassay
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine
pGl: Pyroglutamine
Me: Methyl group
Et: Ethyl group
Bu: Butyl group
Ph: Phenyl group
TC: Thiazolidine-4(R)-carboxamide group Sequence Identification Numbers in the sequence table in the present specification represent the following sequences:

SEQ ID NO:1
The base sequence of a synthetic DNA primer used to amplify cDNA encoding the receptor protein of the present invention by the RT-PCR method.

SEQ ID NO:2
The base sequence of a synthetic DNA primer used to amplify cDNA encoding the receptor protein of the present invention by the RT-PCR method.

SEQ ID NO:3
The base sequence of cDNA from mouse embryonal carcinoma cell line P19 encoding eight amino acid sequences characteristic of the receptor protein of the present invention.

SEQ ID NO:4
The base sequence of cDNA encoding the receptor protein of the present invention.

SEQ ID NO:5
The amino acid sequence of the receptor protein of the present invention.

SEQ ID NO:6
The base sequence of cDNA from frog embryo encoding eight amino acid sequences characteristic of the receptor protein of the present invention.

SEQ ID NO:7
The amino acid sequence of eight amino acid sequences characteristic of the receptor protein of the present invention.

SEQ ID NO:8
The base sequence of a DNA fragment amplified from mouse embryonal carcinoma cell line P19 undergoing nerve induction with retinoic acid by the RT-PCR method using the synthetic DNA of SEQ ID NO:1 and SEQ ID NO:2.

SEQ ID NO:9
The base sequence of a synthetic DNA primer used to amplify cDNA encoding the receptor protein of the present invention by the RT-PCR method.

SEQ ID NO:10
The base sequence of a synthetic DNA primer used to amplify cDNA encoding the receptor protein of the present invention by the RT-PCR method.

EXAMPLES

The present invention is hereinafter described in more detail by means of the following examples, which are not to be construed as limitative to the present invention.

Example 1

Preparation of Poly(A)$^+$ RNA Fraction from Mouse Embryonal Carcinoma Cell Line P19 Undergoing Neuronal Differentiation with Retinoic Acid Mouse embryonal carcinoma cell line ECP19 cells, $10^5$ cells/ml, were inoculated to an α-minimum essential medium containing 10% bovine serum in dishes for *Escherichia coli* cultivation. After retinoic acid (all-trans, produced by Sigma Corporation) was added at $5 \times 10^{-7}$ M, the cells were subjected to suspended culture for 72 hours at 37° C. in the presence of 5% $CO_2$ and 95% air. The cells were then washed with the same medium to remove the retinoic acid, after which they were transferred to a dish for tissue culture, where they were cultured for 3 days. After cultivation, the cells were recovered via centrifugation and treated by the guanidine isothiocyanate method to prepare total RNA [Kaplan, B. B. et al., Biochem. J., 183, 181–184 (1979)] and prepare a poly(A)+ RNA fraction using an mRNA purification kit (produced by Pharmacia).

Example 2 cDNA Amplification by RT-PCR Method Using Poly(A)+ RNA from Mouse Embryonal Carcinoma Cell Line Undergoing Neuronal Differentiation with Retinoic Acid Using 1 µg of poly(A)+ RNA prepared from mouse embryonal carcinoma cell line P19 undergoing neuronal differentiation with retinoic acid as a template, amplification by RT-PCR was conducted. The reaction was carried out using synthetic DNA primers (SEQ ID NO:1 and SEQ ID NO:2), each 100 pM, and the TaKaRa RNA PCR kit (ver. 2) (produced by Takara Shuzo), as directed in the kit manual. Amplification was achieved in 30 cycles of 95° C.×30 seconds, 60° C.×30 seconds and 72° C.×1.5 minutes using a thermal cycler (Perkin-Elmer). The amplification product was detected by 2.0% agarose gel electrophoresis and ethidium bromide staining.

Example 3

Subcloning of RT-PCR Product in Plasmid Vector and Selection of New Candidate Receptor Clones by Decoding of Base Sequence of cDNA Insert The RT-PCR reaction product obtained in Example 2 was separated using 2.0% low-melting agarose gel; after being cut out using a razor, the band portion was subjected to thermal melting, phenol extraction and ethanol precipitation to recover the DNA. The DNA recovered was subcloned into a plasmid vector, as directed in the instruction manual of the TA cloning kit (Invitrogen). After the subcloned DNA was introduced to, and transformed in, $Escherichia\ coli$ JM109 competent cells (produced by Takara Shuzo), clones having a cDNA insert were selected in LB agar medium containing ampicillin, IPTG (isopropyl thio-β-D-galactoside) and X-gal (5-bromo-4-chloro-3-indolyl-β-D-galactoside); the clones showing a white color were separated using a sterilized toothpick to yield transformants of $Escherichia\ coli$ JM109. Each clone was cultured overnight in LB medium containing ampicillin, after which plasmid DNA was prepared using an automatic plasmid extractor (produced by Kurabo). Using a portion of the thus-prepared DNA, Eco RI cleavage was conducted to confirm the size of the cDNA insert. A portion of the remaining DNA was further subjected to RNase treatment and phenol/chloroform extraction, followed by concentration by ethanol precipitation; the resulting concentrate was subjected to base sequencing as described below.

Base sequencing was achieved by reaction using a Dye Deoxy Terminator Cycle Sequencing Kit (produced by ABI) and subsequent decoding using a fluorescent automatic sequencer. The base sequence information obtained was analyzed using DNASIS (produced by Hitachi System Engineering).

The base sequence determined is shown by SEQ ID NO:8.

Homology search based on the base sequence determined demonstrated that the cDNA fragment inserted in the plasmid harbored by the transformant of $Escherichia\ coli$ JM109 encoded a new activin receptor protein resulting from insertion of the 24 bp base sequence shown by SEQ ID NO:3 into a known mouse activin receptor.

Example 4

Cloning of cDNA Containing Entire Coding Region of Receptor Protein from cDNA Library from Mouse Embryonal Carcinoma Cell Line P19 Undergoing Neuronal Differentiation with Retinoic Acid Using 10 µg of poly(A)+ RNA prepared from mouse embryonal carcinoma cell line P19 undergoing neuronal differentiation with retinoic acid in Example 1, in combination with a random 9-mer primer, first strand cDNA was synthesized as directed in the instruction manual of the cDNA Synthesis System Plus (produced by Amersham), followed by synthesis of second strand cDNA, to yield 269 ng of double-stranded cDNA. To both ends of this double-stranded cDNA, an adaptor was ligated using a cDNA rapid adaptor ligation module (produced by Amersham) as directed in the instruction manual of the module. To 75 ng of this ligated double-stranded cDNA, λZAPII vector arm was ligated using a λZAP II/Eco RI/CIAP Treated Vector Kit (produced by Toyobo), as directed in the instruction manual of the kit. Of the resulting cDNA library, $2.1 \times 10^6$ pfu (plaque forming unit) was mixed with $Escherichia\ coli$ XL1-BlueMRF', previously treated with magnesium sulfate, followed by incubation at 37° C. for 15 minutes, after which 0.5% agarose LB was added, and the mixture was sown on 1.5% agar (produced by Wako Pure Chemical Industries) LB plates. On the plates showing plate formation, a nitrocellulose filter was placed to transcribe the plaques thereto. This filter was denatured by alkali treatment, after which it was heated at 80° C. for 3 hours to fix the DNA.

This filter was incubated with the following probe at 42° C. overnight in a buffer containing 50% formamide, 5×SSPE (SSPE; 150 mM NaCl, 10 mM $NaH_2PO_4.H_2O$, 1.25 mM EDTA, pH 7.4), 5×Denhardt's solution, 0.1% SDS (sodium dodecyl sulfate) and 100 µg/ml salmon sperm DNA to cause hybridization. The probe used was prepared by cleaving the DNA fragment (inserted in a plasmid) obtained in Example 3 with Eco RI and recovering the fragment, and was used after labeling by incorporation of [$^{32}$P] dCTP (produced by DuPont) using a random prime DNA labeling kit (produced by Amersham). The filter was washed with 2×SSC (SSC; 150 mM NaCl, 10 mM $NaH_2PO_4.H_2O$) and 0.1% SDS at room temperature for 1 hour and 15 minutes then at 60° C. for 1 hour and 15 minutes, followed by autoradiography at −80° C. to detect hybridizable plaques.

This screening detected 30 independent plaques showing a hybridization signal. Each plaque was picked up and transferred to 5 ml of SM (50 mM Tris-HCl, pH 7.5, 0.1 M NaCl, 7 mM $MgSO_4$, 0.01% gelatin); after vigorous stirring, a portion of the mixture was mixed with $Escherichia\ coli$ XL1-BlueMRF', previously treated with magnesium sulfate, followed by incubation at 37° C. for 15 minutes, after which 0.5% agarose (produced by Pharmacia) LB was added, and the mixture was sown on 1.5% agar (produced by Wako Pure Chemical Industries) LB plates. On these plates, a nylon filter was placed to transcribe the plaques thereto. This filter was denatured by alkali treatment in the same manner as above, after which it was heated at 80° C. for 3 hours to fix the DNA.

These filters were hybridized to the same probe in the same manner as those described above and washed in the same manner as that described above to detect hybridizable plaques.

This screening demonstrated that 28 clones were positive. To determine whether these clones encode a known activin receptor protein or the new receptor protein of the present invention, each plaque was suspended in distilled water to yield template DNA. Using this template DNA in combination with the synthetic DNA primers shown by SEQ ID NO:1 and SEQ ID NO:2, the PCR method was conducted to confirm the length of amplified DNA fragments.

This screening demonstrated that three clones encode the new receptor protein.

The insert of this clone was then cut out using Eco RI; the resulting fragment was subcloned into the Eco RI site of pUC118, after which *Escherichia coli* JM109 was transformed with this plasmid to yield a transformant. The base sequence of the cDNA fragment inserted in the plasmid was then determined. Specifically, using the restriction enzyme sites in the Eco RI fragment, unnecessary portions were removed or a necessary fragment was subcloned to yield a template plasmid for base sequencing.

Base sequencing was achieved by reaction using a Dye Deoxy Terminator Cycle Sequencing Kit (produced by ABI) and subsequent decoding using a fluorescent DNA sequencer (produced by ABI). Data analysis was conducted using DNASIS (produced by Hitachi Software Engineering).

The base sequence determined is shown in FIGS. 3 and 4. This base sequence agreed with the mouse activin receptor type IIA described in Cell, Vol. 65, pp. 973–982 (1991), except for the base sequence shown by SEQ ID NO:3, demonstrating its identity as a new subtype of mouse activin receptor type IIA.

Example 5

Figure 7:
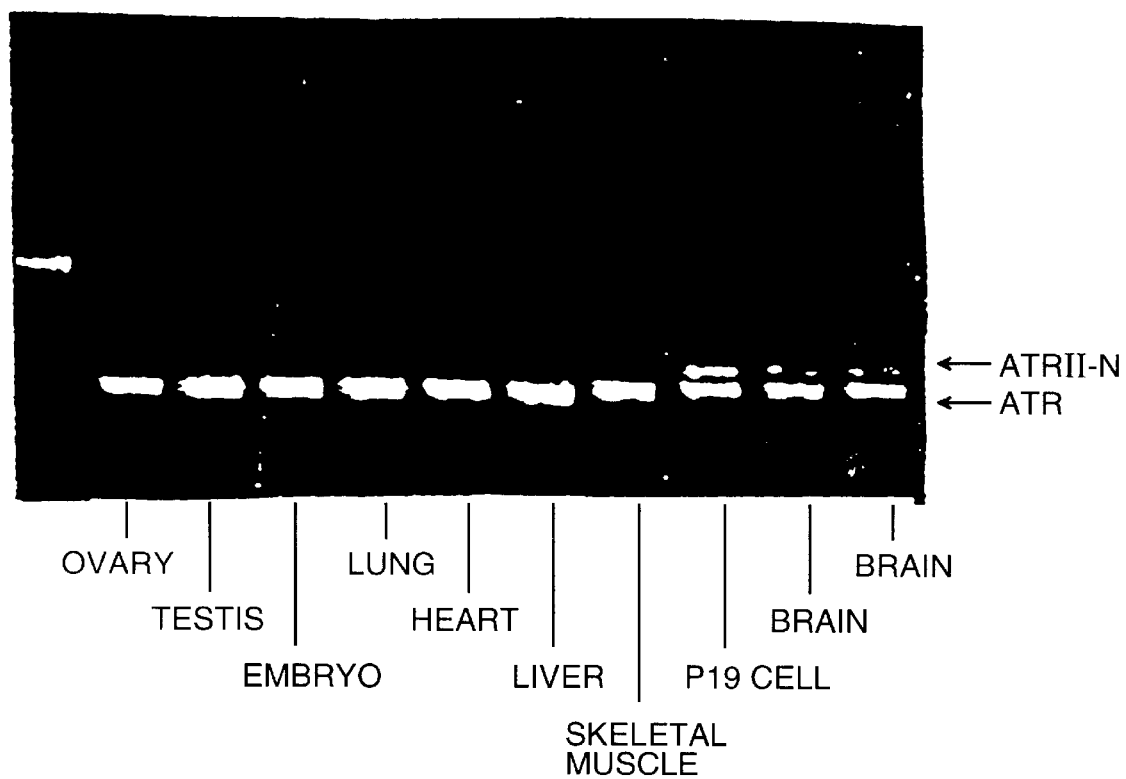
FIG. 7 shows an analysis of expression by the RT-PCR method using poly(A)⁺ RNA from various mouse organs or mouse embryonal carcinoma cell line P19 undergoing neuronal differentiation with retinoic acid. (See Example 5.) The entire base sequence of the cDNA encoding the frog activin receptor type II protein is referenced as SEQ ID NO: 14. The frog activin type II receptor protein is referenced as SEQ ID NO: 15. In the figure, ATR represents an RT-PCR product corresponding to known mouse activin receptor type IIA; ATR IIA-N represents an RT-PCR product corresponding to the new receptor of the present invention.

Detection of Expression by the RT-PCR Method Using Poly(A)$^+$ RNA from Various Mouse Organs Using 1 µg of poly(A)$^+$ RNA prepared from mouse ovary, testes, total embryo, lung, heart, liver, skeletal muscle or brain as a template, amplification by RT-PCR was conducted. The reaction was carried out using synthetic DNA primers (SEQ ID NO:1 and SEQ ID NO:2), each 100 pM, and the TaKaRa RNA PCR kit (ver. 2) (produced by Takara Shuzo), as directed in the kit manual. Amplification was achieved in 30 cycles of 95° C.×30 seconds, 60° C.×30 seconds and 72° C.×1.5 minutes using a thermal cycler (produced by Perkin-Elmer). The amplification product was detected by 2.0% agarose gel electrophoresis and ethidium bromide staining. The results are shown in FIG. 7. The receptor of the present invention was found to be expressed specifically in the brain, as with the mouse embryonal carcinoma cell line P19 undergoing neuronal differentiation with retinoic acid, demonstrating that the receptor of the present invention is expressed specifically in the nervous system.

Example 6 cDNA Amplification by RT-PCR Method Using Poly(A)$^+$ RNA from Human Neuroblastoma Cell Line or Frog Embryo Using 1 µg of commercially available poly(A)$^+$ RNA (produced by Toyo Bouseki) from human neuroblastoma or poly(A)$^+$ RNA from frog embryo as a template, amplification by RT-PCR was conducted. The reaction was carried out using synthetic DNA primers (SEQ ID NO:1 and SEQ ID NO:2 for the human RNA; SEQ ID NO:9 and SEQ ID NO:10 for the frog RNA), each 100 pM, and the TaKaRa RNA PCR kit (ver. 2) (produced by Takara Shuzo), as directed in the kit manual. Amplification was achieved in 30 cycles of 95° C.×30 seconds, 60° C.×30 seconds and 72° C.×1.5 minutes using a thermal cycler (produced by Perkin-Elmer). The amplification product was detected by 2.0% agarose gel electrophoresis and ethidium bromide staining.

Example 7

Subcloning of RT-PCR Product into Plasmid Vector and Selection of New Candidate Receptor Clones by Decoding of Base Sequence of cDNA Insert The RT-PCR reaction product obtained in Example 6 was separated using 1.0% low-melting agarose gel; after being cut out using a razor, the band portion was subjected to thermal melting, phenol extraction and ethanol precipitation to recover the DNA. The DNA recovered was subcloned into a plasmid vector, as directed in the instruction manual of the TA cloning kit (produced by Invitrogen). After the subcloned DNA was introduced to, and transformed in, *Escherichia coli* JM109 competent cells (produced by Takara Shuzo), clones having a cDNA insert were selected in LB agar medium containing ampicillin, IPTG (isopropyl thio-β-D-galactoside) and X-gal (5-bromo-4-chloro-3-indolyl-β-D-galactoside); the clones showing a white color were separated using a sterilized toothpick to yield transformants of *Escherichia coli*. Each clone was cultured overnight in LB medium containing ampicillin, after which plasmid DNA was prepared using an automatic plasmid extractor (produced by Kurabo), and subjected to base sequencing as described below.

Base sequencing was achieved by reaction using a Dye Deoxy Terminator Cycle Sequencing Kit (produced by ABI) and subsequent decoding using a fluorescent automatic sequencer. The base sequence information obtained was analyzed using DNASIS (produced by Hitachi System Engineering).

Homology search based on the base sequence determined demonstrated that the cDNA fragment from the human neuroblastoma cell line agreed with SEQ ID NO:3. The amino acid sequence deduced from this base sequence is shown by SEQ ID NO:7.

The base sequence of the cDNA fragment from frog embryo was determined to be SEQ ID NO:6; the amino acid sequence deduced from the base sequence agreed with SEQ ID NO:7.

The receptor protein and protein-encoding DNA of the present invention can be used as reagents for various purposes, including 1) ligand determination, 2) obtainment of antibodies and antisera, 3) construction of recombinant receptor protein expression systems, 4) development of receptor binding assay systems and screening for pharmaceutical candidate compounds using such expression systems, 5) drug designing based on comparison with structurally similar ligand receptors, 6) preparation of probes and PCR primers for gene diagnosis, and 7) drugs for gene therapy. Elucidation of the structures and natures of activin receptors, in particular, would lead to the development of unique pharmaceuticals that act on these systems.

What is claimed is:

1. An isolated and purified DNA containing a nucleotide sequence encoding a protein comprising SEQ ID NO:7 or a salt thereof.

2. The isolated and purified DNA of claim 1, containing the sequences shown by X'-nucleotide 12 through nucleotide 1571 of SEQ ID NO:4, wherein X' represents ATG or hydrogen.

3. The isolated and purified DNA of claim 1 which contains a nucleotide sequence encoding a protein comprising an amino acid sequence represented by SEQ ID No: 5.

4. A vector containing the DNA of claim 1.

5. An isolated host cell transformed with the vector of claim 4.

6. A method of producing a protein consisting of SEQ ID NO: 5 by culturing a transformant harboring a vector comprising an isolated and purified DNA that encodes a protein consisting of SEQ ID NO: 5 to produce and accumulate the protein in the culture, and collecting said protein or salt thereof.

7. A method of producing a protein consisting of SEQ ID NO: 5 by culturing a transformant harboring a vector comprising an isolated and purified DNA that encodes a protein consisting of SEQ ID NO:5 to produce and accumulate the protein in the culture supernatant or on the transformant's cell membrane, and collecting said protein or salt thereof.

8. A method of producing a protein comprising SEQ ID NO: 5 by culturing a transformant harboring a vector comprising an isolated and purified DNA that encodes a protein comprising SEQ ID NO:5 to produce and accumulate the protein in the culture, and collecting said protein or salt thereof.

9. A method of producing a protein comprising SEQ ID NO: 5 by culturing a transformant harboring a vector comprising an isolated and purified DNA that encodes a protein comprising SEQ ID NO:5 to produce and accumulate the protein in the culture supernatant or on the transformant's cell membrane, and collecting said protein or salt thereof.

* * * * *